United States Patent [19]

Mai et al.

[11] Patent Number: 5,087,564
[45] Date of Patent: Feb. 11, 1992

[54] RELEASE OF RECOMBINANT PEPTIDES FROM POLYPEPTIDES USING V8 ENDOPEPTIDASE

[75] Inventors: Marilyn S. Mai, Ballwin; Michael L. Bittner, Maryland Heights; Sarah R. Braford, Creve Coeur, all of Mo.

[73] Assignee: Monsanto Company, St. Louis, Mo.

[21] Appl. No.: 382,050

[22] Filed: Jul. 18, 1989

Related U.S. Application Data

[63] Continuation of Ser. No. 856,385, May 2, 1986, abandoned, which is a continuation-in-part of Ser. No. 747,135, Jun. 20, 1985, abandoned.

[51] Int. Cl.[5] .................... C12P 21/02; C12N 15/16; C12N 15/70
[52] U.S. Cl. .................... 435/69.7; 435/71.2; 435/320.1; 435/172.3; 435/252.3; 536/27; 530/399; 935/47; 935/51
[58] Field of Search .................. 435/69.1, 71.2, 252.3, 435/320, 172.3, 172.1; 835/48, 51, 47; 536/27

[56] References Cited

U.S. PATENT DOCUMENTS

| | | | |
|---|---|---|---|
| 4,496,544 | 1/1985 | Needleman | 514/13 |
| 4,663,283 | 5/1985 | Kleid et al. | 435/91 |
| 4,704,362 | 11/1987 | Itakura et al. | 435/253 |
| 4,743,679 | 5/1988 | Cohen et al. | 935/47 |
| 4,745,055 | 5/1988 | Schenk et al. | 435/7 |
| 4,745,069 | 5/1988 | Mayne et al. | 435/320.1 |
| 4,749,686 | 6/1988 | Hintze | 514/12 |
| 4,769,327 | 9/1988 | Stephens et al. | 435/68 |

FOREIGN PATENT DOCUMENTS

| | | |
|---|---|---|
| 0035384 | 9/1981 | European Pat. Off. . |
| 0108045 | 5/1984 | European Pat. Off. . |
| 161937 | 5/1985 | European Pat. Off. . |

OTHER PUBLICATIONS

Oikawa et al., *Nature*, 309:724–726, 1984 (Jun.).
Houmard et al. (1972), PNAS, vol. 69(2), pp. 3506–3509.
Keener, S. L. et al., Cloning and Characterization of *recA* Genes from *Proteus vulgaris, Erwinia carotovora, Shigella flexneri,* and *Escherichia coli* B/r, Journal of Bacteriology, Oct. 1984, vol. 160, No. 1, pp. 153–160.
S. Casaregola et al., *Mol. Gen. Genet.*, 185:430 (1981).
S. I. Feinstein et al., *Nucleic Acids Research*, 11:2927 (1983).
T. Horii et al., *Proc. Natl. Acad. Sci. USA*, 77:313 (1980).
K. Itakura et al., *Science*, 198:1056 (1977).
T. Miki et al., *Mol. Gen. Genet.*, 183:25 (1981).

*Primary Examiner*—Richard A. Schwartz
*Assistant Examiner*—Richard M. Lebovitz

[57] ABSTRACT

A method for obtaining heterologous peptides from fusion proteins wherein heterologous peptides include eucaryotic hormones such as atrial peptides. A novel DNA sequence encoding atrial peptide III. Various genes, DNA vectors, endopeptidases and transformed bacteria useful in practicing the method of the present invention.

24 Claims, 10 Drawing Sheets

```
              1     2     3     4     5     6     7     8     9    10
        glu - phe - glu - ser - ser - cys - phe - gly - gly - arg - ile - asp - arg -
    5'- A-A-T-C-G-A-A-T-C-C-A-G-C-T-G-T-T-C-G-G-C-G-G-A-G-A-A-T-C-G-A-T-A-G-A-
        EcoRI                 PvuII                              ClaI
    3'-     G-C-T-T-A-G-G-T-C-G-A-C-A-A-G-C-C-G-C-C-T-C-T-T-A-G-C-T-A-T-C-T 11    12    13    14    15    16    17    18    19    20
        ile - gly - ala - gln - ser - gly - leu - gly - cys - asn -
        A-T-C-G-G-C-G-C-C-C-A-A-T-C-A-G-G-C-C-T-T-G-G-T-G-T-A-A-C
                  NarI              StuI
        T-A-G-C-C-G-C-G-G-G-T-T-A-G-T-C-C-G-G-A-A-C-C-C-A-C-A-T-G 21    22    23    24
        ser - phe - arg - tyr - ter - ter - ter
        T-C-T-T-T-C-C-G-T-T-A-C-T-T-A-A-T-G-A-T-C-T-A-G-A-G-                -3'
                                                XbaI          EcoRI
        A-G-A-A-A-G-G-C-A-A-T-G-A-T-T-A-C-T-A-G-A-T-C-T-C-T-T-A-A -5'
```

FIG. 1.

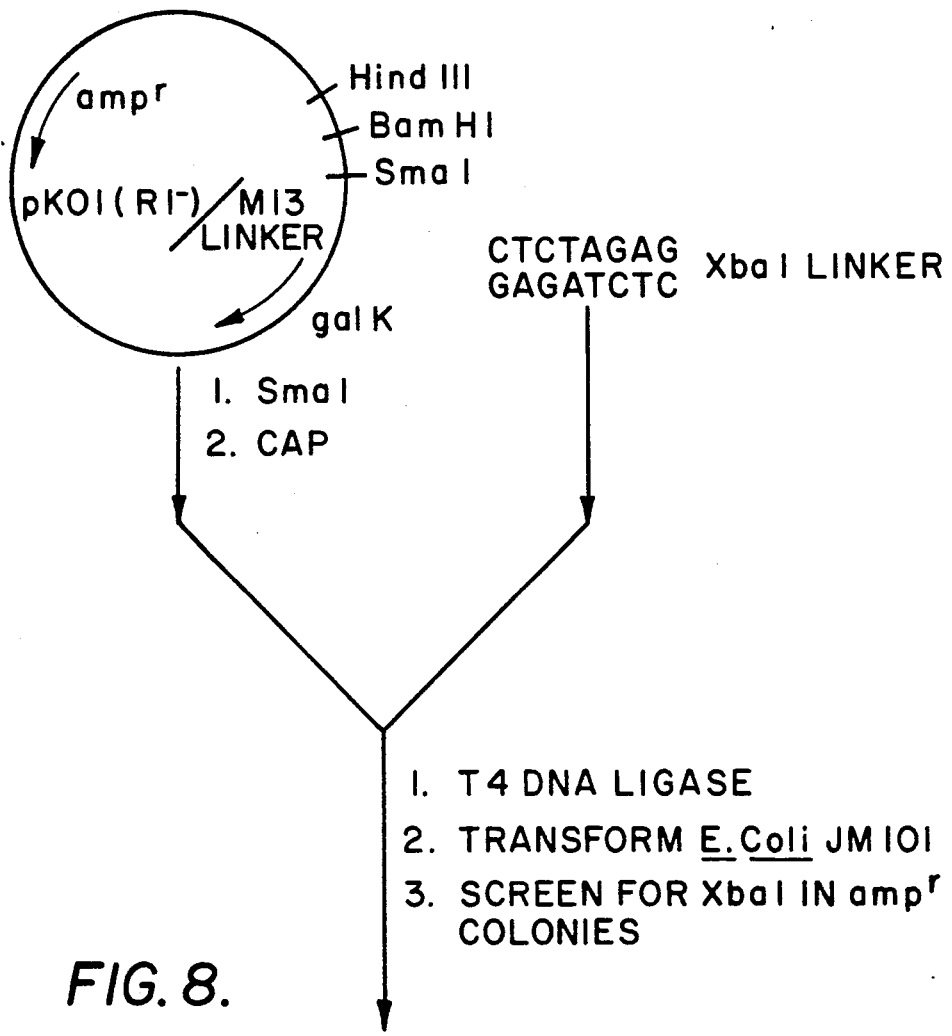
FIG. 8.
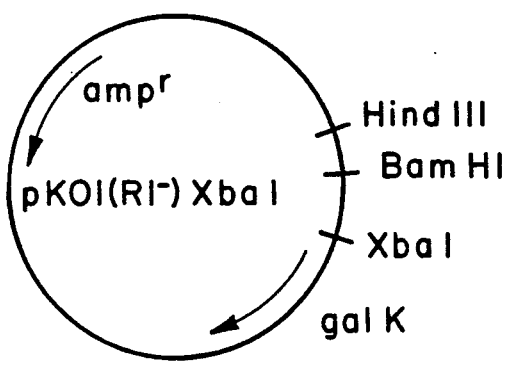

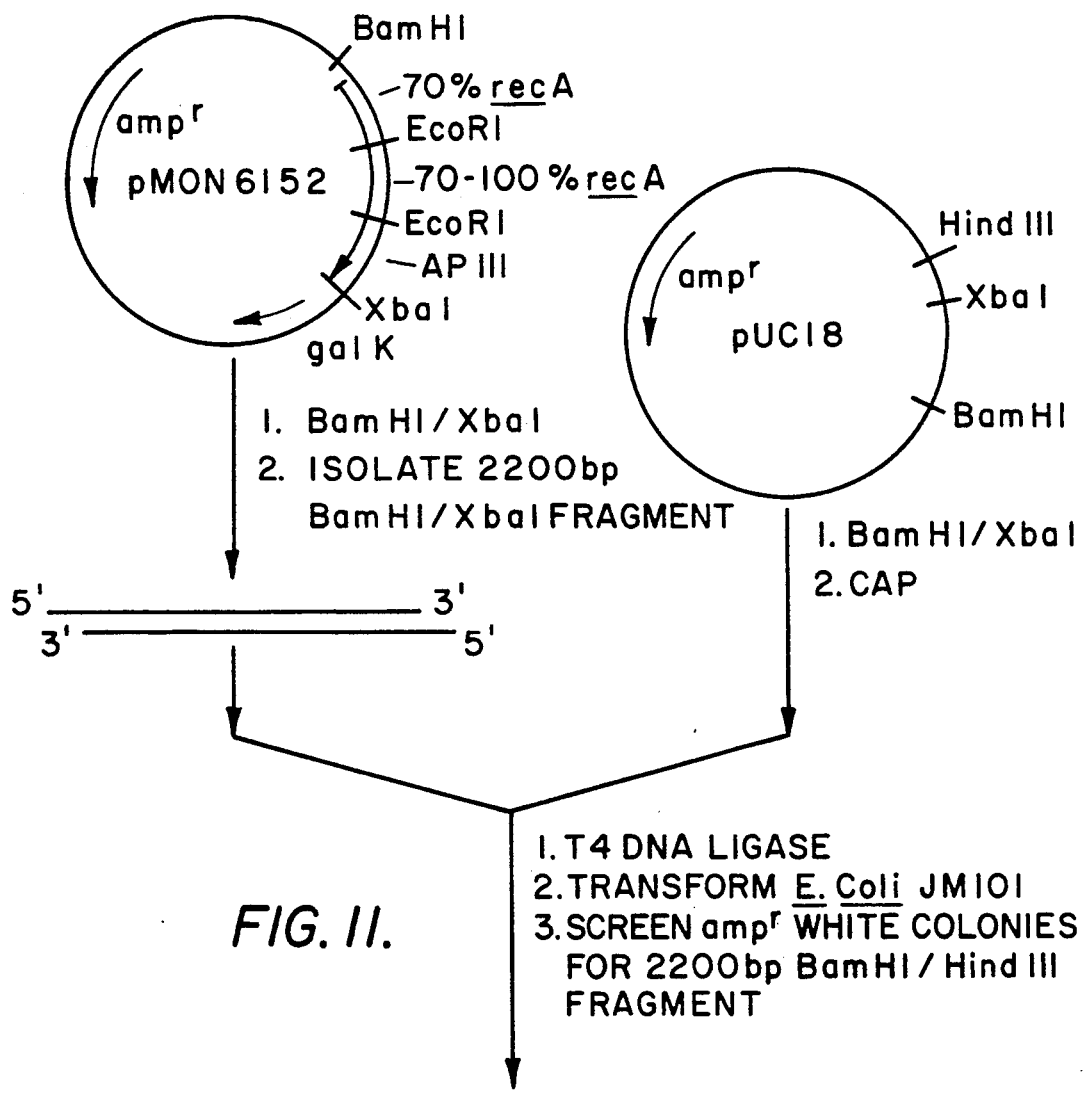
FIG. 11.
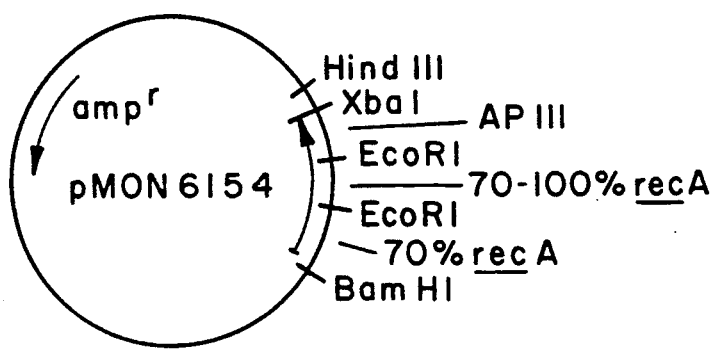

RELEASE OF RECOMBINANT PEPTIDES FROM POLYPEPTIDES USING V8 ENDOPEPTIDASE

This is continuation of application Ser. No. 856,385, filed May 2, 1986, now abandoned which is a continuation-in-part of application Ser. No. 747,135, filed June 20, 1985, now abandoned.

TECHNICAL FIELD

The present invention relates to methods and compositions for obtaining heterologous peptides from fusion proteins. In one important embodiment, the present invention relates to the cleavage of bacterially-produced fusion proteins containing an amino acid sequence specific for *Staphylococcus aureus* V8 protease cleavage at the junction of two peptides which together comprise the bacterially produced fusion protein. In another important embodiment this invention relates to production of atrial peptides as a bacterially produced fusion protein and the subsequent isolation of said atrial peptides employing the cleavage methods of the present invention. In yet another embodiment, this invention relates to the creation of novel DNA coding sequences for atrial peptides.

BACKGROUND OF THE INVENTION

Advances in recombinant DNA technology and genetic engineering have provided a means for producing in bacteria eucaryotic proteins of clinical and hence economic importance. The employment of bacterial cells as factories (e.g. host cells) for eucaryotic protein production has become especially attractive for eucaryotic proteins of limited availability. One important example of limited availability is human hormones. The problem of obtaining tissue is further magnified by the fact that a given tissue extract yields very low quantities of a given hormone.

The use of bacteria as host cells for eucaryotic protein production currently involves first isolating or synthesizing the gene or DNA sequence encoding the desired peptide and, second, incorporating the gene or DNA sequence into the genome of the host cell in a manner which allows for expression of the DNA sequence or gene and resultant protein production, accumulation and/or secretion.

Differences between eucaryotic and procaryotic cellular control of gene expression and protein production, however, have given rise to several obstacles which must be overcome if given eucaryotic proteins, peptides or fragments thereof are to be produced in bacteria efficiently and at commercially-attractive levels.

In eucaryotes, many mature proteins are first translated as pre-proteins; i.e., polypeptides comprised of the mature proteins's sequence fused to a leader or signal sequence. Eucaryotic mRNA encodes the entire preprotein, which is processed after translation to remove the leader sequence and provide the mature protein. Although eucaryotic cells are equipped to specifically process such pre-proteins into mature proteins, bacterial cells are generally not able to recognize the processing signals present in eucaryotic proteins. Thus, if complete complementary DNA (cDNA) transcripts of eucaryotic mRNA are employed as the DNA sequences for expression in bacteria, the pre-protein, not the mature protein, is obtained. It is possible to convert pre-proteins to mature proteins in vitro, but not without significant expense.

In the event that the DNA sequence encoding the mature protein is used for mature protein expression in bacteria, this sequence will be lacking the eucaryotic translation and post-translation processing signals usually contained within the DNA for the leader sequence. Therefore, for expression of cloned eucaryotic genes or other heterologous DNA sequences in bacterial systems, it has proven desirable to employ bacterial control signals for reasons of efficiency and because eucaryotic signals may not be recognized by a bacterial host cell.

The term "heterologous DNA" is defined herein as DNA at least a portion of which is not normally contained within the genome of the host cell. Examples of heterologous DNA include, but are not limited to, viral and eucaryotic genes, gene fragments, alleles and synthetic DNA sequences. The term "heterologous protein" or "heterologous polypeptide" is defined herein as a protein or polypeptide at least a portion of which is not normally encoded within the genome of the host cell. The term "genome" refers to all DNA (chromosomal and extrachromosomal) contained within a specified cell.

The bacterial control signals include a promoter, which signals the initiation of transcription, and translation control signals comprising a ribosome binding site, a translation start signal and a translation stop signal. All of these signals except the translation stop signal must be situated in front of the eucaryotic gene or other DNA to be expressed.

The art has adopted several approaches to expressing heterologous DNA (e.g. eucaryotic genes) in bacteria. In one approach, the translation start signal, ATG, under the control of a bacterial promoter, is located immediately preceding the DNA sequence encoding a heterologous (e.g. eucaryotic) protein. Expression of such a DNA construct results in production of eucaryotic proteins free from endogenous proteins or protein fragments herein defined as "direct" protein production. The proteins so produced, however, typically contain an amino(N)-terminal methionine as the ATG translation start signal is also a methionine codon. See Harris, T.J.R. (1983). Thus, unless the desired mature protein begins with methionine, the protein will now have an N-terminus altered by inclusion of that methionine residue.

Additionally, the direct production approach has not generally been successfully applied to production of heterologous (e.g. eucaryotic) peptides, wherein a "peptide" is defined as a protein containing fewer than 100 amino acids or proteins having a molecular weight of less than about 10,000 daltons. The problem with direct production of heterologous peptides lies in the tendency of bacteria, such as *E. coli*, to recognize eucaryotic peptides produced therein as foreign and, thus, proceed to degrade these peptides as soon as these peptides are produced or shortly thereafter. See R.K. Craig and L. Hall (1983); Itakura et al. (1977). Furthermore, it has been found that structural features inherent in the nucleic acid (DNA or RNA) sequence coding for a heterologous protein or peptide product often interfere with efficient heterologous protein or peptide production (i.e. translation) in bacteria. Hence, an alternate approach to production of such heterologous peptides as eucaryotic peptide hormones has been developed.

In one alternate approach, the DNA segment encoding the desired protein or peptide is ligated to endogenous DNA encoding all or part of a bacterial protein under the control of its bacterial promoter. The endogenous bacterial DNA necessarily also contains the ribosome binding site and translation start signal. In ligation, the DNA encoding the desired protein or peptide must be inserted in-frame with the endogenous transcription and translation control signals and endogenous DNA coding sequences, and in the same orientation. Expression of the ligated DNA provides a fusion protein comprising the heterologous protein or peptide linked (e.g. fused) to a whole or partial bacterial protein. Ideally, such fusion constructs should provide a relatively high and/or stable level of fusion protein accumulation in the bacterial host cell and/or high level of secretion by the host cell.

Production of heterologous proteins and peptides in bacteria has been reported to be aided by fusion of the desired heterologous product peptide or protein to an endogenous protein or fragment thereof. For example, the endogenous protein may serve to enhance transcription and/or translation, Craig and Hall (1983), or, may be employed to aid in purification of desired product. See Sessenfeld, H.M. and Brewer, S.J. (1984) (use of polyarginine binding to ion exchange columns); Germino, J. and Bastia, D. (1984) ($\beta$-galactosidase affinity column). In addition, especially in Bacillus and yeast systems, fusion of a desired protein or peptide to an endogenously secreted protein or a signal peptide may result in the secretion of mature protein product into the host growth media free from intracellular proteins and endogenous protein sequences.

Furthermore, the fusion protein approach is useful in protecting otherwise foreign protein or peptide products from intracellular degradation. See Itakura, K. et al. (1977) and R.K. Craig and L. Hall (1983). Fusion proteins engineered for protective purposes can employ endogenous polypeptide sequences at either the amino or carboxy terminus of the heterologous peptide.

In all cases, final isolation of the bacterially-produced eucaryotic peptide must be achieved by site-specific enzymatic or chemical cleavage at the endogenous-eucaryotic peptide fusion site, herein referred to as "junction site", or by selective degradation of the endogenous polypeptide sequences. The junction site may contain a single peptide bond that links the heterologous (e.g. eucaryotic) peptide to the endogenous protein or contain a series of peptide bonds joining the heterologous peptide to the endogenous protein. Most commonly, bacterially produced fusion proteins are constructed so that the endogenous peptide or fragment thereof comprises the N-terminal portion of the fusion protein with the heterologous peptide comprising the C-terminal portion. Such constructions allow for the simultaneous release of the endogenous peptide/protein and the N-terminal methionine following cleavage at the junction site.

Examples of site-specific release of eucaryotic peptides from bacterially produced fusion proteins by chemical means include the following: Stephien et al. (1983) (proinsulin fused to yeast galactokinase); Tanaka et al. (1982) ($\alpha$-neo-endorphin fused to E. coli $\beta$-galactosidase); Goeddel et al. (1979) (insulin A and B chain fused to E. coli $\beta$-galactosidase); Itakura et al. (1977) (somatostatin fused to E. coli $\beta$-galactosidase). In all the foregoing examples, the chemical cyanogen bromide was employed to cleave the fusion protein and release the desired peptide. Cleavage of a protein or polypeptide is defined herein as the hydrolysis of a peptide bond in a protein or polypeptide. Cyanogen bromide hydrolyzes peptide bonds at the carboxy-side of methionine residues under acid conditions. Thus, site-specific cleavage of a fusion protein requires the presence of a methionine residue immediately upstream and adjacent to the N-terminal amino acid of the desired peptide and an absence of methionine residues in the internal amino acid sequence of the desired peptide.

The disadvantages of chemical hydrolysis include the harsh acid conditions under which cleavage occurs, such conditions possible causing undesirable modifications in the product peptide, the need to know the amino acid sequence of the product peptide to insure against internal cleavage sites, and the observation that the specificity of some chemical cleavages depend largely upon amino acids immediately adjacent to the bond being cleaved.

As an alternative to chemical cleavage, several investigators have reported the use of enzymes, peptidases, to achieve release of the desired peptide product from bacterially produced fusion proteins. Peptidases are generally defined as enzymes which catalyze the hydrolysis (cleavage) of peptide bonds.

One specific class of peptidases employed to date has been the endopeptidases. These peptidases are particularly well suited for use in release of a desired peptide from fusion proteins comprising an endogenous (carrier) protein at the N-terminus of the fusion protein and the desired peptide at the C-terminus. Endopeptidases recognize either specific single amino acids or specific amino acid sequences present within the internal amino acid sequence of a polypeptide and then cleave the peptide bond preferably on the carboxyside of a given amino acid. The amino acid or amino acid sequence specifically recognized and cleaved by a given endopeptidase shall henceforth be referred to as a "trigger amino acid" or "trigger sequence", respectively, or collectively as a "trigger signal."

Examples of various endopeptidases employed to cleave bacterially produced fusion proteins to release a desired peptide include the following: International Patent Application publication number WO84/00380 (published Feb. 9, 1981) (trypsin to release human calcitonin from a trypophan promoter/operator system); European Patent Application publication number 35,384 (published Sept. 9, 1981) (suggested use of enterokinase); Nagai and Thogersen (1984) (Factor Xa to release human $\beta$-globin from a $\lambda$CII protein); Germino, J. and Bastia, D. (1984) (microbial collagenase to release R6K replication initiator from $\beta$-galactosidase); Shine et al. (1980) (trypsin ro release $\beta$-endorphin from $\beta$-galactosidases); Rutter, W.J. (1979) (suggested use of enterokinase to cleave fusion proteins); European Patent Application publication number 161,937 (published Nov. 21, 1985) (Factor Xa to release $\beta$-globin from $\lambda$CII, human calcitonin glycine from CAT, and myosin light chain from $\lambda$CII).

As in the case of chemical cleavage, the trigger signal must constitute the junction bond or site if release of the mature peptide from the bacterially produced fusion protein is to be achieved. Unlike chemical cleavage, however, the vast number of endopeptidases available affords a greater choice of trigger signals for potential use in peptide release.

The decision of which trigger signal or endopeptidase is best employed to achieve release is governed by several factors most of which are tied to the specific bacterial expression system employed to produce the fusion protein and the amino acid sequence of the desired peptide itself. As will be discussed herein, there exists a significant degree of unpredictability in the art. This predictability is best understood by reviewing some of the factors which affect selection of a given endopeptidase and subsequent cleavage of fusion proteins by endopeptidases.

The major factors affecting the choice of the trigger signal and hence endopeptidase employed is whether the complete amino acid sequence of the desired peptide is known and whether the resultant fusion protein allows endopeptidase cleavage at the junction site. If the amino acid sequence is known, a trigger signal can be chosen which does not occur in the desired peptide thereby avoiding unwanted hydrolysis of the desired peptide. Once chosen, a DNA sequence encoding the trigger signal must be synthesized and inserted at the junction site in a manner which will not significantly interfere with expression, production, accumulation and/or purification of the fusion protein. For example, when inserting a given trigger signal at the junction site, the insertion must not disturb the in-frame reading of the coding sequences for the endogenous and heterologous peptides. In preparing the fusion protein for endopeptidase cleavage, it is necessary that the trigger signal be available or exposed for optimum cleavage and release of the desired peptide, and that the cleavage conditions be such that the desired peptide is not irreparably damaged by the reaction conditions necessary for cleavage. Additionally, it is generally desirable that trigger signals are not present within the endogenous protein so that a clean release of the desired peptide can be achieved. The maintenance of the integrity of the endogenous protein is often required for a subsequent commercially feasible purification of the desired peptide.

In the event that the precise amino acid sequence of the desired peptide is not known, the trigger signal should comprise an amino acid sequence of sufficient complexity so as to diminish the likelihood of a similar sequence being contained within the desired peptide.

As an additional consideration when employing endopeptidases, it has been determined that for some endopeptidases, amino acids in the vicinity of the site of hydrolysis will be recognized and/or bound by the enzyme. These "peripheral" amino acids, in some instances, can increase the catalytic efficiency or binding affinity of the enzyme and thus effect the susceptibility of a peptide containing a trigger signal to hydrolysis by a given endopeptidase. European Patent Application publication number 35,384 (published Sept. 9, 1981). Conversely, these peripheral amino acids may decrease the hydrolytic efficiency of a given endopeptidase. Behrens and Brown (1976); Austen and Smith (1976); Houmard and Drapeau (1972a). The presence of peripheral amino acids at or near the junction site should, therefore, be considered as to their effects, if known, on the trigger signal. The effect of peripheral amino acids on specific endopeptidase cleavage is, however, unknown for many of the described endopeptidases. Thus, the ambiguities in the context (e.g. structure) and content (e.g. linear sequence) of any given endopeptidase trigger signal render the operability of a trigger signal for release of a desired peptide from a fusion protein unpredictable in most instances.

In summary, construction of a specific fusion protein with a given trigger signal providing for site-specific release of a desired peptide must accommodate a plurality of factors affecting not only endopeptidase cleavage but polypeptide expression, production and accumulation as well. A fusion protein system applicable to the production of a wide variety of desired proteins or peptides does not currently exist which will satisfy all these factors.

As indicated earlier, one important embodiment of the claimed invention involves production of atrial peptides as a bacterially produced fusion protein, cleavage of the fusion protein and recovery of the product. Mammalian atria contain peptides that exert potent effects on kidney function and regional vascular resistance. These peptides, originally extracted from rat atria and exerting natriuretic, diuretic and smooth muscle relaxant (e.g. vasodilating) activities are currently referred to as atrial peptides.

Rat atrial extracts have been fractionated into low molecular weight fractions (<10,000 daltons) and high molecular weight fractions (20,000–30,000 daltons) both of which relaxed smooth muscle in vitro and were potent natriuretic agents when administered intravenously to rats. See Currie et al. (1983). Trippodo et al. (1982) found natriuretic activity in the overall molecular weight range of 3,600 to 44,000 daltons and in peptide fractions of both higher molecular weight range of 36,000–44,000 daltons and a lower molecular weight in the range of 3,600–5,500 daltons.

Efforts devoted to the purification and chemical characterization of atrial peptides have been hampered by the scarcity of material available from atrial homogenates and by the apparent heterogeneity of the biologically active factor. The amino acid sequence of several atrial peptides is now known, see U.S. Pat. No. 4,496,544; U.S. Pat. No. 4,508,712; European Patent Application publication number 116,784 (published 8/29/84); Seidah, N.G. et al. (1984); deBold et al. (1983); deBold and Flynn (1983). The low molecular weight nature (<10,000 daltons) of many of the atrial peptides identified to date will undoubtedly require the fusion protein approach for production in bacteria.

Accordingly, it is an object of the present invention to provide endopeptidases useful in achieving optimum cleavage of a bacterially produced fusion protein to release a desired heterologous peptide.

It is another object of the present invention to provide methods for cleaving bacterially produced fusion proteins to achieve the release of desired heterologous peptides in their mature form.

It is yet another object of the invention to provide methods for producing in bacteria atrial peptides having useful natriuretic, diuretic and/or vasodilating activity.

It is a further object of the present invention to provide methods for producing in bacteria, fusion proteins containing atrial peptides which have useful natriuretic, diuretic and/or vasodilating activity.

It is still a further object of the present invention to provide methods for producing in bacteria fusion proteins containing atrial peptides wherein said atrial peptides can be enzymatically released from said fusion protein in their mature form.

It is yet a further object of the present invention to provide fusion proteins which allow for high level of production, in bacteria, of atrial peptides and affords site-specific cleavage and release of atrial peptides from the fusion protein.

SUMMARY OF THE INVENTION

The present invention provides methods for producing a heterologous peptide in bacteria. Also provided are novel DNA sequences encoding heterologous peptides and various genes, DNA vectors and transformed bacteria useful in practicing the method of the present invention. One method involves expressing in bacteria genomic DNA encoding a fusion protein, the fusion protein comprising a heterologous peptide linked to an endogenous protein at a junction site, wherein both the endogenous protein and junction site have an endopeptidase cleavage site; recovering the fusion protein; treating the fusion protein with a suitable endopeptidase such that the endogenous cleavage site at the junction site is preferentially cleaved while the endopeptidase cleavage site in the endogenous protein is substantially intact; and obtaining therefrom the desired heterologous peptide.

The present invention also provides heterologous polypeptides comprising a recA protein or portion thereof, an endopeptidase cleavage site and an atrial peptide.

Heterologous peptides obtainable by the method of the present inventions are atrial peptides. The novel DNA sequences encode atrial peptides.

BRIEF DESCRIPTION OF THE DRAWINGS

In the following diagrammatic representations, the directional arrows represent the 5' to 3' orientation of the DNA coding sequences. Relevant restriction endonuclease sites are also shown. The DNA regions so marked are for purposes of diagrammatic representation only and are not drawn to scale.

FIG. 1 shows the complete dsDNA sequence encoding APIII prepared for insertion into the vector M13mp9 along with the corresponding amino acid sequence. "1" denotes the start of the mature APIII peptide.

FIG. 8 depicts the construction of pK01(RI⁻)/XbaI comprising a pK01(RI⁻)/M13 linker vector having inserted therein at the SmaI restriction site an XbaI restriction site.

FIG. 11 depicts the construction of pMON6154 comprising a pUC18 vector having inserted therein at the BamHI restriction site DNA encoding the recA-Glu-APIII gene.

DETAILED DESCRIPTION OF THE INVENTION

Figures 2, 3:
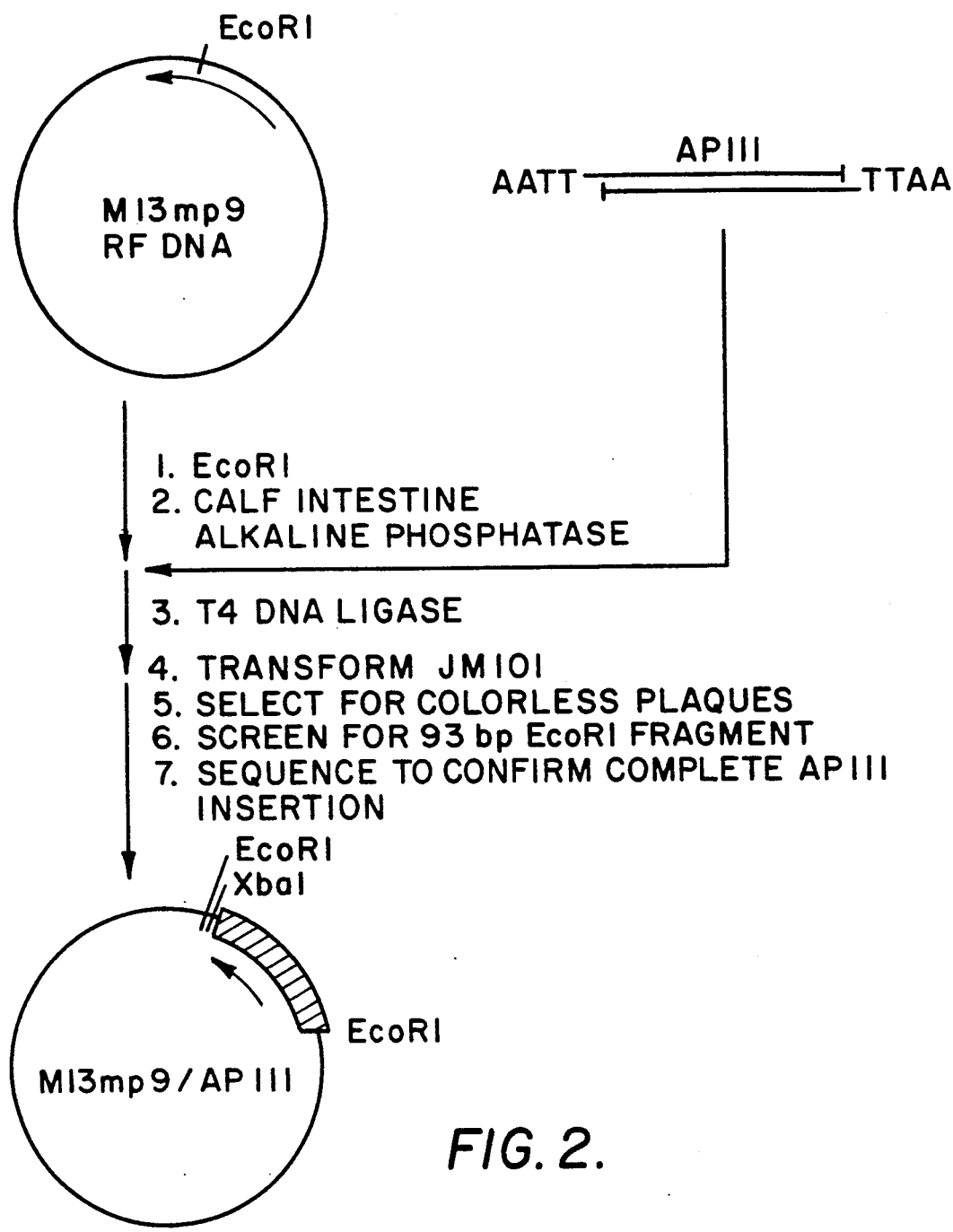
FIG. 2 depicts the construction of M13mp9/APIII comprising m13mp9 carrying an APIII DNA coding sequence. The hatched box represents the DNA coding sequence for APIII.
FIG. 3 depicts the construction of the synthetic double-stranded APIII DNA coding sequence. The , symbols show the place where ligation occurs.

The present invention provides a method for obtaining heterologous peptides from fusion proteins by site-specific cleavage with an endopeptidase. Suitable heterologous peptides include eucaryotic hormones, one example of which are atrial peptides. Suitable endopeptidases include, but are not limited to, Trypsin, Plasmin, Enterokinase, Kallikrein, Urokinase, Tissue Plasminogen Activator, Clostripain, Chymotrypsin, Pepsin, Chymosin, Collagenase, Russell's Viper Venom Protease, Post-proline cleaving enzyme, *Staphyloccus aureus* strain V8 extracellular protease, herein referred to as "V8 protease", blood coagulation factor Xa, herein referred to as "factor Xa," and thrombin, wherein V8 protesase, thrombin and factor Xa are the preferred endopeptidases.

V8 protease is an endopeptidase which cleaves specifically the peptide bonds on the carboxy-terminal side of either aspartate (Asp) or glutamate (Glu) residues. See Houmard and Drapeau (1972a and b). Due to its single amino acid specificity, V8 protease has been used extensively in peptide mapping. See McWhereter, C. A. et al. (1984); Hausinger and Howard (1982); Johnson, J.S. (1983); Cleveland et al. (1977). In the present description, the term V8 protease refers to any V8 protease derived from a bacterial or any recombinant or synthetic source.

V8 protease has two pH optima, pH 4.0 and 7.8, and is active in both urea and sodium dodecyl sulfate (SDS), reagents often employed to solubilize proteins. These cleavage properties render V8 protease attractive for use in cleavage of bacterially produced fusion proteins.

One study by Austen and Smith (1976), which examined the ability of V8 protease to cleave Glu when this residue was at or near either the N- or C-terminus of a peptide indicated that no cleavage occurs when Glu is within two residues of the N-terminus or within two to three residues from the C-terminus. The authors interpreted these findings as suggesting that the peptide must be bound to the enzyme over a region extending several residues on either side of the potentially susceptible bond. The single observed cleavage at Glu when the Glu residue was within two residues of the N-terminus was attributed by these authors to be possibly due to the increased polar character of the residues on the C-terminal end of the peptide studied. V8 protease enzymatic activity, however, is generally believed not to be affected either adversely or positively by neighboring amino acid residues with the possible exception of Asp-X wherein X is cysteic acid, and Glu-X wherein X is glutamic acid or proline which have not been observed to be cleaved by V8 protease. See Houmard and Drapeau (1972a) and (1972b); Behrens and Brown (1976); Austen and Smith (1976).

Employment of V8 protease in fusion protein cleavage systems, however, necessarily requires that the desired peptide not contain any trigger amino acids, herein Glu or Asp, and/or that any internal Glu or Asp residues be unavailable for V8 protease cleavage under the cleavage conditions employed. It is additionally desirable that the endogenous protein not contain any trigger amino acids and/or that any internal Glu or Asp residues be unavailable for V8 protease cleavage under the cleavage conditions employed.

Blood coagulation factor Xa is a member of the serine protease group. In vivo, factor Xa activates prothrombin to thrombin by specific limited proteolysis at the bonds Arg (274)-Thr (275) and Arg (323)-Ile (324). In prothrombin, both cleavage sites are preceded by the same tetrapeptide, Ile-Glu-Gly-Arg, which has been proposed as a determinant of factor Xa substrate recognition. (Magnusson, S. et al., 1975). Some of the peptide sequences known to be cleaved by factor Xa are also described in EPA publication number 161,939 (published Nov. 21, 1985). It appears that the structure required for recognition by factor Xa is determined by the local sequence at the cleavage site (EPA 161,939).

The DNA sequence of the present invention may code for any cleavage site which is specifically cleaved by factor Xa including all of the specific factor Xa cleavage sequences (i.e. trigger signals) previously described. In one preferred embodiment, a novel factor Xa trigger signal is described comprising the sequence $NH_2$-Phe-Glu-Gly-Arg-COOH.

As is the case with V8 protease and thrombin, discussed below, the specific nucleotides present in the gene coding for a fusion protein containing a factor Xa trigger signal will depend upon the particular amino acid sequence of the trigger signal and the genetic code. Thus, in view of the redundancy (i.e. degeneracy) of the genetic code, a plurality of different DNA sequences can be used to code for a single trigger signal. A particular DNA sequence can be chosen having regard to host codon usage preferences and/or to facilitate DNA manipulations, for instance to provide convenient restriction endonuclease sites.

Treatment of proteins including fusion proteins with factor Xa results in substantially exclusive cleavage at the peptide bond following the arginine (Arg) amino acid residue of the factor Xa trigger signal to liberate a protein fragment or desired peptide in native form. The term "native form" refers to a polypeptide or peptide comprising the amino acid sequence thereof without additional amino acid residues, e.g. an N-terminal methionine or N-terminal host protein amino acid residues.

Thrombin is a serine proteinase that catalyzes the cleavage of certain arginyl and lysyl bonds. Thrombin has been found in the blood plasma in all classes of vertebrates and is an important enzyme in blood coagulation. The naturally occurring substrate for thrombin is fibrinogen which is cleaved by thrombin at an arginylglycyl bond to form fibrin. (Magnusson, S., 1971). Trigger signals thus far identified for thrombin include Glu-Gly-Arg. (Magnusson, 1971).

The choice of which endogenous protein sequence or fragment thereof to employ in construction a gene for production in bacteria of a fusion protein containing the desired peptide depends upon several factors. A "gene" is defined herein as a DNA sequence encoding the protein product to be expressed and the necessary transcription and translation control signals for production of the desired protein product in a given host cell. These factors include, but are not limited to, the availability of the chosen endogenous gene sequence or fragment thereof, the strength of the attendant promoter, facility with which the expression of said gene may be induced and/or controlled in a given host cell, size of the expressed endogenous product or fragment thereof, the ability to solubilize the fusion protein produced in a given host to accommodate subsequent cleavage and release of the desired peptide and/or ability to monitor expression of the endogenous DNA sequence. Additionally, the chosen endogenous protein or fragment thereof should yield both a stable and high level accumulation of the desired protein or peptide product when joined thereto to yield a fusion protein. Furthermore, the resultant fusion protein must be either soluble or solubilizable so that subsequent site-specific enzymatic release of the desired protein or peptide can be achieved.

A number of bacterial genes which are readily expressed at high levels in bacteria are known to those skilled in the art and include, without limitation, the chloramphenicol acetyl transferase (CAT) gene, the $\beta$-galactosidase gene (lac Z) and recA gene. Such genes exemplify endogenous genes which can be used as fusion carriers with the desired protein or peptide product.

In one embodiment, the recA gene or fragments thereof was employed as a fusion carrier for production of such peptides as atrial peptides. The use of a recA gene to affect production of atrial peptides by means of a fusion protein comprising recA or a fragment thereof and an atrial peptide has heretofore not been disclosed. Feinstein, S. et al. (1983) describes the use of a recA promoter to directly express in bacteria human interferon species and the use of a gene construct comprising, in part, a recA promoter, ribosome binding site and first three codons of the recA DNA coding sequence to produce in bacteria a recA-$\beta$-interferon "fusion-like" protein. The term "fusion-like" protein is used to denote the limited amount of recA protein (e.g. three amino acids) present in the $\beta$-interferon containing product protein. EPA publication number 108,045 (published May 9, 1984) and commonly assigned to Monsanto Company, describes the use of a recA promoter/operator to directly express somatostatin in bacteria. This EPA published application also describes the production in bacteria of a recA-somatostatin fusion protein comprising either 70% or 90% of the recA protein and 100% of the somatostatin peptide. We have determined that both the 70% and 90% recA fusion constructs are inoperative for production in bacteria of recA-atrial peptide fusion proteins as the products produced in accordance with these teachings yield an insoluble fusion protein hence precluding subsequent enzymatic cleavage to release the desired atrial peptide.

None of the previously described art teaches or suggests an economic and efficient means for producing large quantities of atrial peptides in bacteria for both scientific and therapeutic uses.

The selection of the recA protein as an endogenous protein carrier in the fusion protein systems described herein was also made based upon certain advantageous physical properties of the recA protein. Specifically, the recA protein is a highly negatively charged protein. The highly charged nature of the recA protein affords a major advantage in the subsequent purification of bacterially produced fusion proteins containing recA or portions thereof which retain the net negative charge. For example, such conventional methodologies as anion exchange chromatography can be employed to isolate recA proteins from substantially all other bacterial proteins.

In one embodiment of the present invention, V8 protease was chosen to specifically release an atrial peptide from a bacterially produced fusion comprising the entire recA protein of bacteria joined to an atrial peptide by a V8 protease-specific trigger signal. Atrial peptides contain no glutamic acid residues and only one aspartic acid at position nine. See U.S. Pat. No. 4,496,544. The recA protein, however, contains numerous (i.e. approximately 31) glutamic acid residues.

Notwithstanding the presence of an internal Asp residue in the desired peptide and numerous Glu residues in the recA protein, we proceeded to attempt the specific release of an atrial peptide from a bacterially produced recA-atrial peptide fusion protein. "Internal" is herein defined as any amino acid not at the N- or C-terminus of the protein. In so doing, we discovered that V8 protease preferentially cleaves a Glu trigger signal sequence present at the junction site, thereby promoting an early release of the desired peptide prior to cleavage of internal Glu residues present in the recA protein.

The present discovery is significant since it provides a method for specifically cleaving recA-atrial peptide fusion proteins containing a Glu residue in a trigger signal present at the junction site. Furthermore, the observed early release of the desired peptide from said fusion protein represents an unexpected result as one would have predicted a simultaneous cleavage at Glu residues within the recA protein thereby masking the specific release of the desired atrial peptide, and possible impeding subsequent isolation of the desired atrial peptide essentially free from the recA protein or fragments thereof. Indeed, cleavage at the internal Glu (V8 protease) sites does eventually occur if the V8 protease cleavage reaction is allowed to proceed to completion. The methods described herein thereby provide a means for specifically or preferentially releasing such desired peptides as atrial peptides from bacterially produced fusion proteins comprising recA. The endogenous protein (e.g. recA) is thus defined herein as remaining substantially intact wherein the desired heterologous peptide can be distinguished from endogenous protein or fragments thereof following endopeptidase cleavage of the fusion protein.

While applicants do not wish to be bound by the following theory of mechanism, it is believed that the conformation of the bacterially produced recA-containing fusion proteins renders the V protease trigger signal present at the junction site available for endopeptidase cleavage while, at least initially, rendering internal trigger amino acids unavailable for cleavage by V8 protease. It is understood that the unavailability of the internal recA trigger amino acids can result from such structural features as stearic hinderance and/or from kinetic properties associated with the recA-V8 protease interactions. It is furthermore believed that such selective availability of V8 trigger amino acids at the junction site will result from any heterologous peptide fused to a rec A protein or fragment thereof by a junction site containing a V8 protease trigger amino acid.

In one of the preferred embodiments, the method of the present invention is employed to generate atrial peptide I, III or IV (API, APIII or APIV, respectively) (see U.S. Pat. No. 4,496,544 and EPA publication number 116,784) from a bacterially produced recA-containing fusion protein, free from other atrial peptide species. The ability to produce a single atrial peptide species has tremendous import for determining the precise bioreactivity of said species and for obtaining commercial quantities of atrial peptides. Additionally, once the bioreactivity of such atrial peptide species is determined, it is considered feasible to generate peptide variants which would further increase their bioreactivity. Such variants can be generated by nucleotide or amino acid deletion, substitution and/or addition in accordance with techniques described herein and known to those skilled in the art. The production of atrial peptide variants by the method of the present invention are considered to be within the scope of the appended claims.

In its broadest embodiment, the present invention is a refinement in the use of recombinant DNA technology to produce heterologous peptides in bacteria. Thus, the description of the present invention presupposes knowledge of the basic techniques employed in recombinant DNA technology to isolate and clone DNA sequences encoding peptides and proteins, the rearrangement or altering of cloned DNA sequences, and the expression of cloned or modified DNA sequences in transformed microorganisms. Such techniques are within the skill of the art. See e.g. Maniatis et al. (1982).

Isolation and Construction of Heterologous DNA

Production of heterologous (e.g. eucaryotic) peptides in bacteria requires the isolation or synthesis of a DNA sequence encoding the desired peptide. Procedures for isolating DNA sequences and for either chemically or enzymatically synthesizing DNA sequences are well known to those skilled in the art.

It has been found that both E. coli and yeast exhibit various codon preferences. See Craig, R.K. and Hall, L. (1983); Fiers, W. et al. (1976); Ikemura, T. (1982). Thus, to achieve optimum translation of a heterologous mRNA sequence, it may be desirable to substitute those codons preferred by the host cell employed.

In a preferred embodiment of the present invention, a novel DNA sequence encoding APIII was constructed containing preferred codons of both E. coli and yeast cells which, furthermore, allow introduction of restriction endonuclease cleavage sites useful in the manipulation and screening of this DNA sequence. Briefly, a novel DNA sequence encoding the 24 primary amino acid structure of atrial peptide III (APIII) was synthetically produced, as described more fully below. The novel DNA coding sequence of the 72 base pairs (bp) was constructed taking into account both E. coli and yeast host cell codon preferences. The coding part of the sequence was preceded by a codon for glutamic acid providing a recognition site for cleavage of the peptide from a fusion protein with V8 protease. The coding part of the sequence was immediately followed by at least one translation termination codon. The recognition sites for EcoRI and XbaI restriction endonucleases were introduced into the polynucleotide sequence at sites indicated in FIG. 1 to facilitate recombinant manipulation and subsequent monitoring of the synthetic DNA. Thus, the inclusion of these restriction sites is optional. Similarly, alternate and/or additional restriction endonuclease sites may be introduced.

In order to assemble a double-stranded DNA (dsDNA) fragment encoding the APIII peptide shown in FIG. 1, six complementary and partially overlapping synthetic oligonucleotides were synthesized and subsequently annealed to form a 93 bp oligonucleotide under appropriate conditions, as described more fully below and shown in FIG. 3.

After a heterologous DNA sequence containing the codons for the desired polypeptide is obtained, it may be desirable to make certain modifications in the nucleotide sequence of the molecule. For example, if the molecule has been produced by reverse transcription from a messenger RNA (mRNA) template, in lieu of chemical synthesis, it will often contain at least a portion of the DNA encoding the leader sequence of the pre-protein. Thus, it may be necessary to remove all of the leader sequence DNA prior to the first codon of the desired protein.

If not already present, at least one translation stop signal is introduced after the codon for the C-terminal amino acid of the desired peptide. Examples of translation stop signals include the deoxynucleotide triplets (i.e. codons) TAA, TGA and TAG.

As described below, recombinant DNA techniques and/or chemical synthesis were employed to construct a heterologous DNA sequence containing sequentially a glutamic acid codon or the codons for a factor Xa or thrombin trigger signal, the codons for the desired peptide and at least one translation stop signal codon adjacent to the codon for the C-terminal amino acid of the desired peptide.

In constructing the desired heterologous DNA coding sequence, deletions, additions and/or substitutions in any of the amino acid codons within a given heterologous DNA sequence may be made so that a "variant" peptide can be expressed in the process of the present invention. A variant peptide is defined herein as having single or multiple amino acid deletions, substitutions and/or additions as compared to the naturally occurring amino acid sequence of a given peptide. Because these variant peptides have an amino acid sequence essentially the same as that of a naturally occurring peptide, their biological activity is not diminished to an intolerable degree. Construction and expression of variant peptides may be desirable in order to achieve increased fusion protein accumulation, increased peptide and/or fusion protein stability, to facilitate peptide and/or fusion protein purification, and/or to optimize biological activity.

The above modifications of the DNA molecule encoding the desired polypeptide can be accomplished using restriction enzymes, exonucleases, endonucleases, etc. by techniques known in the art. See Maniatis, et al. (1982). The general techniques of oligonucleotide-directed site-specific mutagenesis can also be employed to effect the above modifications in the structure or sequence of the DNA molecule and are known to those of skill in the art. See Zoller & Smith (1982); Zoller & Smith (1983); Norris et al. (1983).

After multiple copies of the desired heterologous DNA sequence are obtained, these sequences may be removed from the recombinant vectors and inserted into an expression system for production and isolation of the desired heterologous peptide as described more fully below. Modifications of the heterologous DNA sequence, by methods known to those skilled in the art, may be made prior to insertion of these DNA sequences into an expression vector, during said insertion and/or following said insertion.

As previously described, production of fusion proteins by bacteria is achieved by the site-specific insertion of the DNA sequence encoding the desired peptide into or immediately downstream from the DNA encoding an endogenous protein or fragment thereof under the control of a bacterial promoter where the endogenous DNA sequence and promoter are carried on an expression vector. Thus, the desired heterologous gene contains DNA sequences encoding an endogenous protein or fragment thereof, an endopeptidase trigger signal and the desired heterologous peptide.

As previously discussed, the choice of which endogenous gene to employ depends on several factors such as the ability to produce in the host cell a highly expressed, soluble protein when coupled with the desired heterologous peptide.

In one preferred embodiment of the present invention, the recA gene of $E.$ $coli$ carried on an expression vector was used as the endogenous DNA sequence to which the desired peptide DNA coding sequence was fused. The recA gene of $E.$ $coli$ is involved in important cellular functions such as genetic recombination, in post replication repair, and in a number of other cellular functions such as mutagenesis, phage induction and cell division. See Sancar, A. and Rupp, D. (1979); Witkin, E.M. (1976). Functional and/or chemical homologs of the $E.$ $coli$ recA protein have been described in other bacterial genera such as Proteus (e.g. $Proteus$ $vulgaris$), Erwinia (e.g. $Erwinia$ $carotovora$) and Shigella (e.g. $Shigella$ $flexneri$), Keener, S. et al. (1984). A recA "homolog" is herein understood to comprise a protein, the gene of which is contained within the genome of bacteria other than $E.$ $coli$, and which protein is characterized as possessing the following characteristics: it functions as a DNA repair enzyme (e.g. an ability to restore resistance to ultra-violet killing in recA$^-$ $E.$ $coli$), and/or shares substantial DNA or amino acid sequence homology with the $E.$ $coli$ recA protein and/or is a highly negatively charged protein having a conformation which allows preferred cleavage at a junction site comprising a V8 protease trigger signal. These homologs which possess substantially the same physical-chemical and/or functional properties of the $E.$ $coli$ recA protein are believed to constitute equivalents of the $E.$ $coli$ recA protein specifically described herein. (Keener, S. et al. 1984).

The recA gene of $E.$ $coli$ is normally repressed by the product of the lexA gene but can become induced by treatments with substances such as naladixic, mitomycin C or ultra violet radiation, all of which damage DNA. Treatment of $E.$ $coli$ with these substances stimulates the recA protein, which is present at low, residual levels, to cleave its repressor and undergo induction. After induction, the recA protein becomes one of the major proteins in the cell, indicating that the combination of a recA promoter and ribosome binding site is an efficient one for inducible expression. See Feinstein, S. et al (1983). The inducible nature of the recA promoter is advantageous in cases where constitutive expression of a cloned gene at such high levels would be harmful to the cell or undesirable for purposes of optimizing purification of a desired recA fusion protein.

Furthermore, any bacteria strain which is recA$^+$ can be employed for production of recA fusion proteins. Such bacteria include $Proteus$ $mirabilis$ (Eitner et al., 1982) and $E.$ $coli$ wherein $E.$ $coli$ are preferred host organisms. The more preferred strains of $E.$ $coli$ are both recA$^+$ and lexA$^+$ as these strains provide for an inducible control of recA fusion protein production. Examples of such preferred $E.$ $coli$ host strains include $E.$ $coli$ MM294 and $E.$ $coli$ JM101, wherein $E.$ $coli$ JM101 constitutes the most preferred host cell for recA fusion protein production. Both of these strains may be obtained from the American Type Culture Collection (ATCC), Rockville, Md. under ATCC accession numbers 33625 and 33876, respectively. Thus, when employing a fusion protein expression vector which codes for a recA homolog, equivalent bacterial host cells selected from, for example, such gram negative bacteria as Enterobacteriaceae, Erwinia, Shigella, Salmonella and Klebsiella, containing a gene for the recA homolog can be employed. The more preferred host cells would contain functional genes for both the recA homolog and recA homolog repressor.

We have discovered that the production in bacteria of a soluble recA-atrial peptide fusion protein requires employment of the entire (i.e. 100%) recA DNA coding sequence. This finding is significant as prior descriptions of the employment of the recA promoter and DNA coding sequences have suggested that use of greater than 70% of the recA DNA coding sequence yields an insoluble fusion protein product in bacterial cell hosts. See EPA 108045 (published May 9, 1984).

The method of the present invention, described more fully below, provides a means for producing in bacteria high levels (e.g. approximately 10 to 30% of the total cell protein) of a stably accumulated heterologous peptide (e.g. atrial peptide) which can be purified to yield a potent natriuretic and/or smooth muscle relaxant agent.

Cloning of Heterologous DNA

In accordance with recombinant DNA techniques, once the desired heterologous DNA sequence is obtained, the sequence is then inserted into an appropriate cloning vector which provides a means for replicating the DNA sequence. Any appropriate cloning vector, preferably containing a marker function, may be used, for example E. coli plasmid vectors which include Col El, Hershfield et al. (1974); pBR322, Bolivar et al. (1977); pBR325, Soberon et al. (1978); and pkc7, Rao et al. (1979); and E. coli bacteriophase vectors which include Charon AL47.1, Loenen et al. (1980); and M13mp8 and M13mp9, Messing et al. (1982). The general techniques for inserting said DNA sequence into a cloning vector to create a recombinant vector are within the skill of the art. See Maniatis et al. (1982).

In the examples of the present invention, M13mp8 and M13mp9, described by Messing et al. (1982), and pUC18, pBR327, pBR322 and pK01 were chosen as the cloning vectors.

The M13mp9 and M13mp8 vectors, hereinafter referred to as the M13 vector or vectors, allow for isolation of recombinant vectors in both double-stranded (ds) or replicative form (RF) and single-stranded (ss) DNA forms. Isolation of RF DNA recombinant vectors facilitates the subsequent insertion of the replicated desired DNA sequences into expression vectors. Alternatively, isolation of the single-stranded form of these recombinant vectors facilitates isolation of recombinant vectors which contain the desired DNA sequence in a proper 5' to 3' orientation for expression, the creation of any DNA sequence modification by such techniques as oligonucleotide-directed site-specific mutagenesis, and facilitates DNA sequence analysis. Additionally, these M13 vectors can accommodate DNA fragments or genes up to 4kb in length which insures the cloning of a typical, entire, eucaryotic gene sequence.

The marker function employed in the M13 vector, as described by Messing et al. (1982), involves the enzyme for β-galactosidase. Specifically, the desired heterologous DNA sequence is inserted into the linker preceding the lacZ gene fragment carried on the M13 vector which disrupts the normal complementation of the lacZ gene carried on the M13 vector with the partial lacZ gene fragment carried on the chromosomal DNA of the host cell (e.g. E. coli JM101) so that said host is no longer capable of metabolizing lactose present in the bacterial growth medium. E. coli infected with M13 vectors which do not have a foreign gene sequence inserted into the vector born lacZ gene fragment are capable of metabolizing lactose present in the bacterial growth medium and yield characteristic blue plaques when the bacteria are grown on agar containing 1×YT medium comprising 0.8% (w/v) tryptone, 0.5% (w/v) yeast extract, 0.5% (w/v) NaCl and a color indicator for β-galactosidase. The plaque coloration of E. coli infected with recombinant vectors carrying an inserted heterologous DNA sequence in the M13 lacZ gene fragment is clear or colorless when the bacteria are grown on said medium. Hence, positive insertion of the heterologous DNA sequence into these cloning vectors is identified by colorless plaque formation following infection of the E. coli host cell with the recombinant vector.

The marker functions on the pBR322, pBR327, pUC18 and pK01 cloning vectors are identified by a preliminary screen for antibiotic resistance and/or colony coloration, as described more fully below, and then restriction endonuclease analysis to confirm the insertion of the desired DNA coding sequences into the vectors, as described more fully below.

Figure 5:
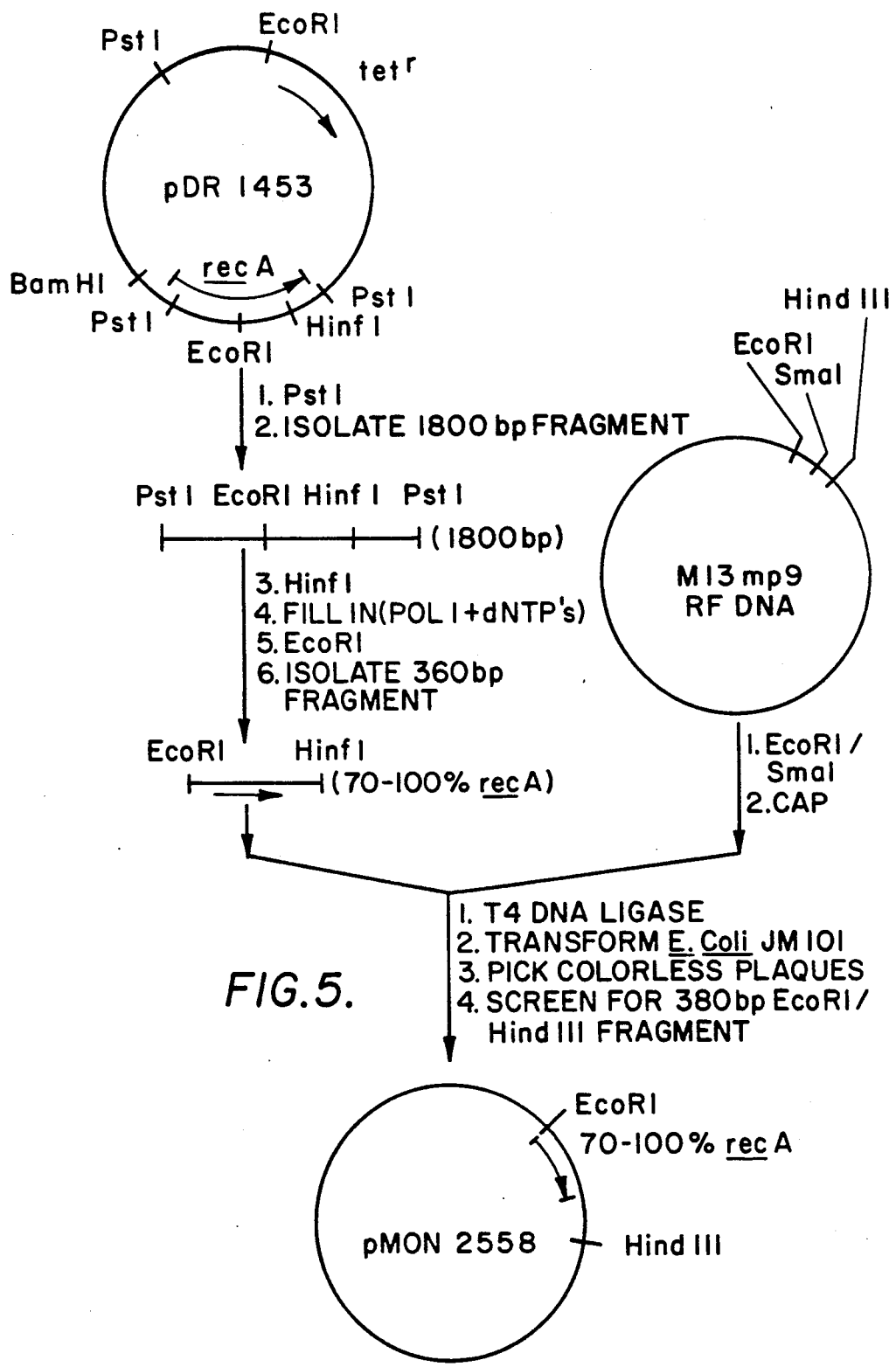
FIG. 5 depicts the construction of pMON2558 comprising a m13mp9 vector having inserted therein at the EcoRI/SmaI restriction site DNA encoding 70-100% recA.
Figure 6:
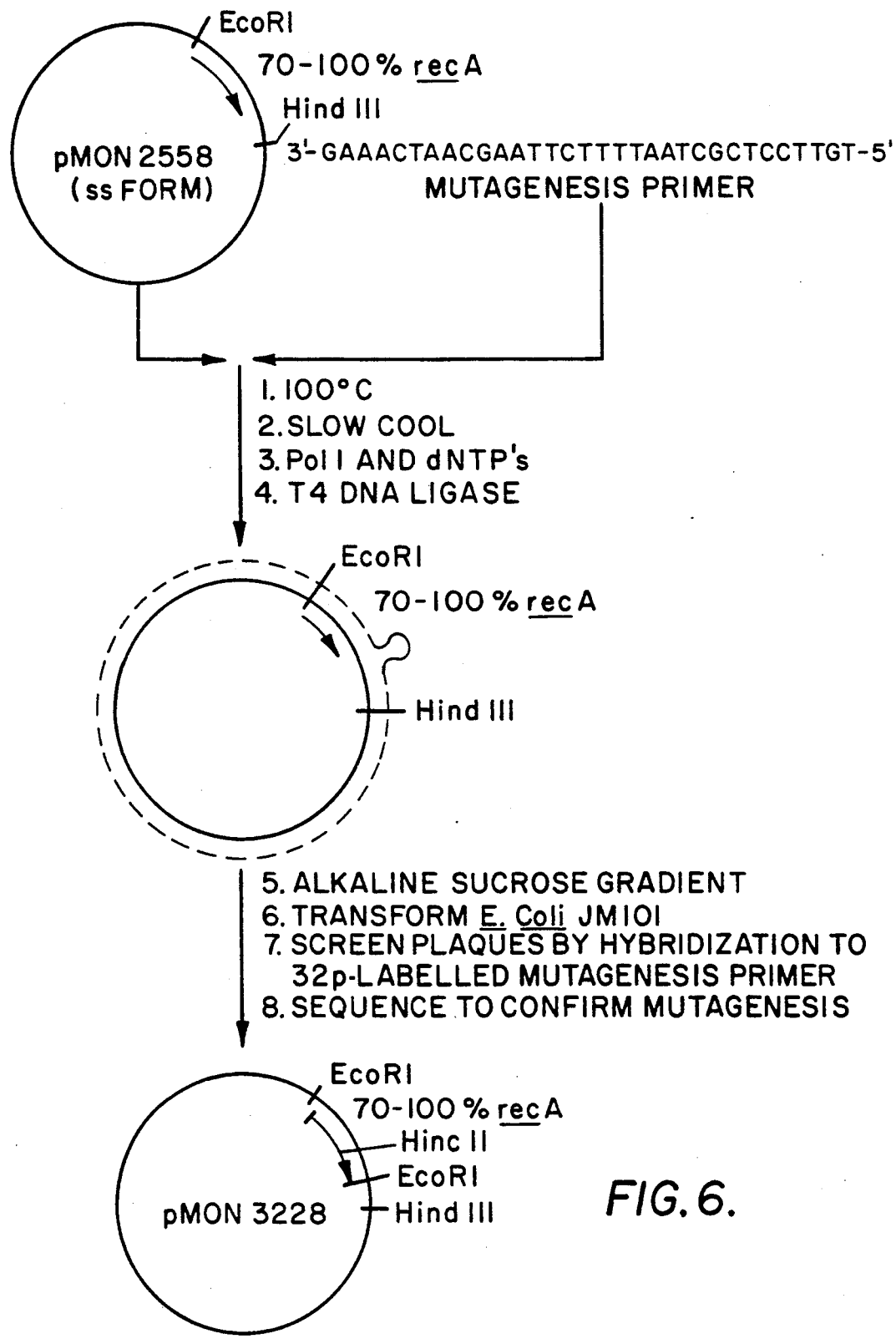
FIG. 6 depicts the creation of an EcoRI restriction site at the 3'-end of the 70-100% recA DNA coding sequence by oligonucleotide-directed site-specific mutagenesis.
Figure 9:
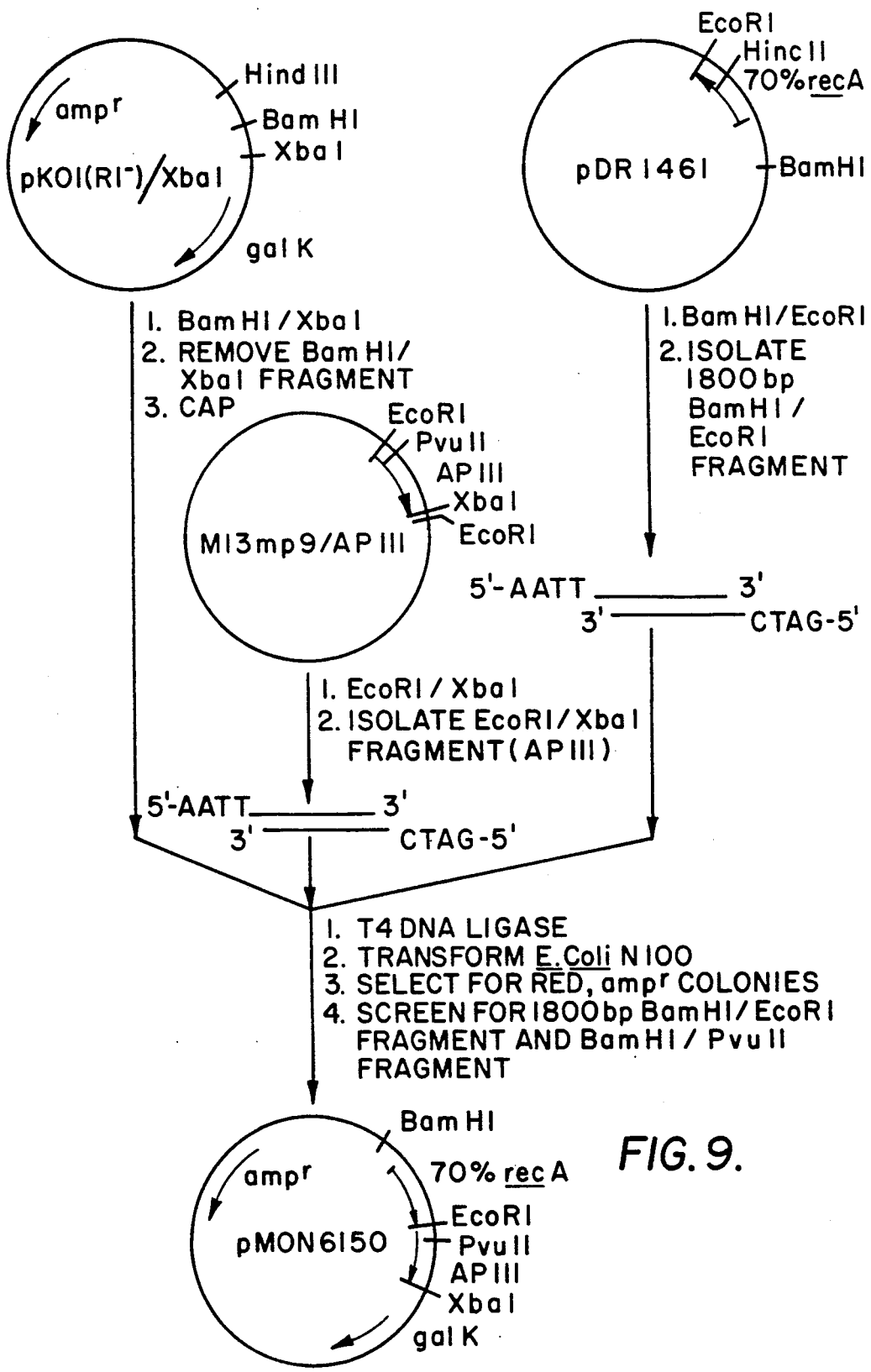
FIG. 9 depicts the construction of pMON6150 comprising a pK01(RI⁻)/XbaI vector having inserted therein at the XbaI restriction site a DNA sequence encoding APIII and having inserted therein at the BamHI restriction site a DNA sequence encoding 70% recA.

In a preferred embodiment, DNA encoding the C-terminal 70-100% of the recA protein, herein referred to as 70-100% recA, was inserted into RF DNA of the M13 vector as shown in FIG. 5 to create a recombinant cloning vector, pMON2558, as described more fully below in the examples. Oligonucleotide-directed site-specific mutagenesis was then employed as shown in FIG. 6 and described more fully below to introduce an EcoRI restriction site at the 3'-end of the recA DNA coding sequence to create recombinant cloning vector pMON3228. Said site was introduced to facilitate subsequent cloning of the 70-100% recA to create expression vector pMON6152 as shown in FIG. 9.

Figure 4:
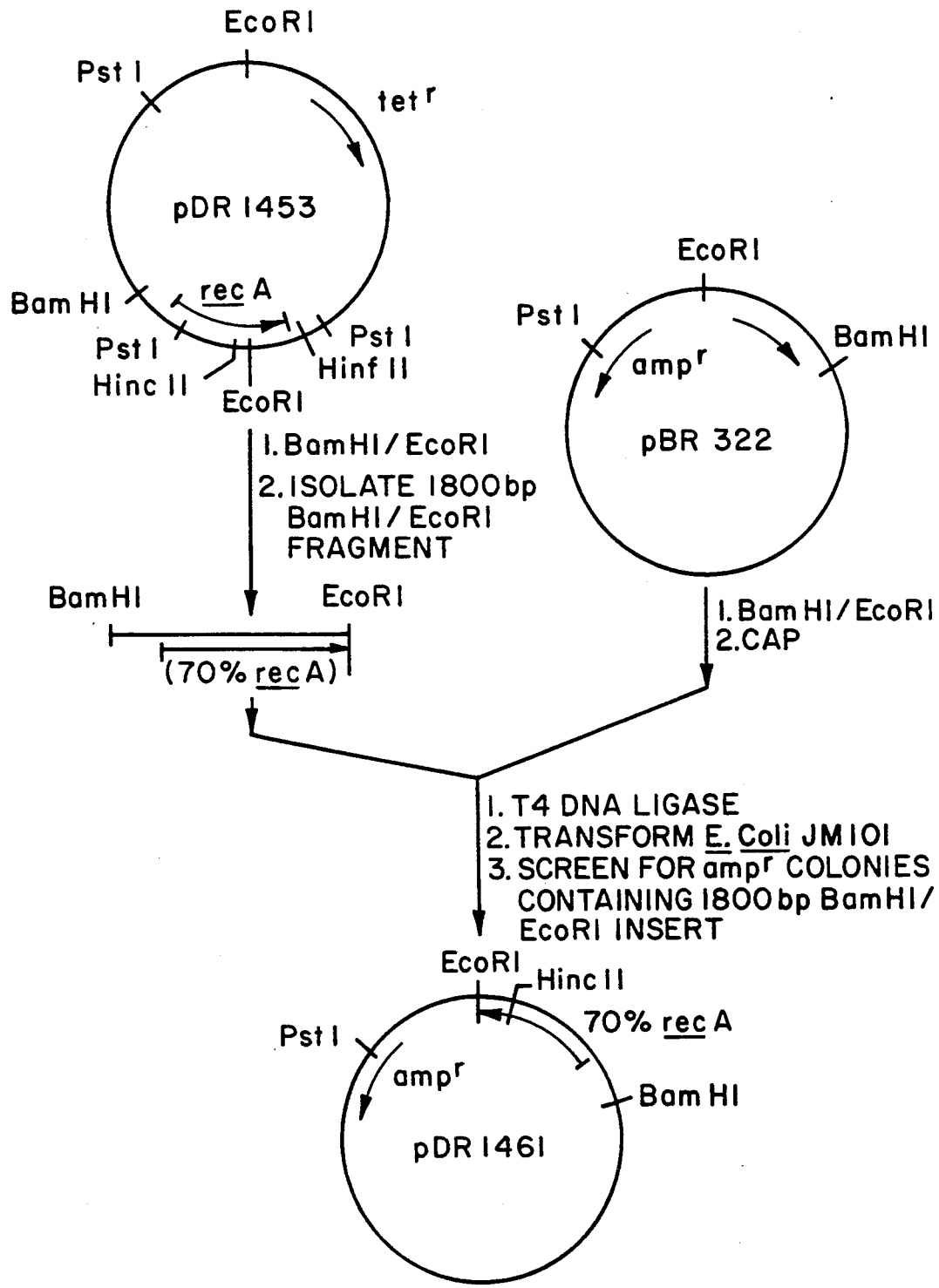
FIG. 4 depicts the construction of pMON1461 comprising a pBR322 plasmid having inserted therein at the EcoRI/BamHI restriction sites DNA encoding 70% recA.

The DNA encoding the recA promoter, ribosome binding site and N-terminal 70% of the recA gene product, collectively referred to herein as 70% recA, was isolated as shown in FIG. 4 below and cloned into a pBR322 cloning vector to create recombinant cloning vector pDR1461 as shown in FIG. 4 and as described more fully below.

In a preferred embodiment, the synthetic APIII DNA coding sequence shown in FIG. 1 was inserted into the unique EcoRI site in M13mp9 to create an APIII containing recombinant cloning vector as shown in FIG. 2. The APIII insertion was confirmed by transfecting E. coli JM101 with the recombinant cloning vector in accordance with the method described by Messing et al. (1983), selecting colorless plaques and then isolating single-stranded recombinant phage DNA in accordance with the method described by Messing et al. (1983), the relevant portions of which are incorporated by reference hereto. The single-stranded phage DNA was then sequenced by the dideoxy chain termination method described by Sanger et al. (1977) to verify the insertion of the complete APIII DNA coding sequence.

Subsequent to cloning the DNA sequences encoding the desired portions of a preferred fusion gene, these sequences can be replicated and numerous copies generated by propagation of the respective recombinant cloning vector by methods known to those skilled in the art and referenced above. These heterologous DNA sequences can be inserted into any appropriate expression vector for production in bacteria of the desired heterologous polypeptides (e.g. fusion proteins).

Production of Fusion Proteins Containing Glu Trigger Signal

As described previously, an appropriate expression vector should contain the necessary transcription and translation signals for production of a heterologous protein in the chosen host cell along with a marker function for identification of those expression vectors into which the desired heterologous DNA sequence has been inserted. By use of a procaryotic expression vector, the recombinant DNA sequences can be added to the genetic complement of a procaryotic organism via transduction, transformation or transfection (collectively referred to herein as "transformation") and the organism can then be cultured under conditions (generally governed by the promoter and host employed) that cause the desired polypeptide to be produced. Thus, the "genomic" DNA of the organisms used in this invention contains both chromosomal and episomal DNA.

A number of expression vectors have been described for heterologous gene expression and heterologous protein production in procaryotic host cells and are known to those skilled in the art. These expression vectors include expression systems in which the promoter contained therein provides for either constitutive or inducible gene expression.

In one preferred embodiment of the present invention, a pKO1 vector obtained from Dr. Martin Rosenberg, National Institutes of Health (Bethesda, Md.) and described in Chirikjian, A. and Papas, T. (1981) was employed as an expression vector. pKO1 is a pBR plasmid derivative which carries an *E. coli* galactokinase gene. The galactokinase gene (galK) product is readily expressed and stably accumulated in *E. coli* N100 transformed with a pKO1 plasmid in which a promoter has been inserted upstream from the galK gene and can serve as a marker for transformation by a number of assays. Rosenberg et al (1968). *E. coli* transformed with pKO1 form red colonies on galactose MacConkey agar whereas non-transformed colonies are white. Alternatively, the gene product may be identified as a discrete band when transformed *E. coli* lysates are subjected to polyacrylamide gel electrophoresis (PAGE) or by an enzymatic assay analysis by assaying for the phosphorylation of galactose.

Figure 10:
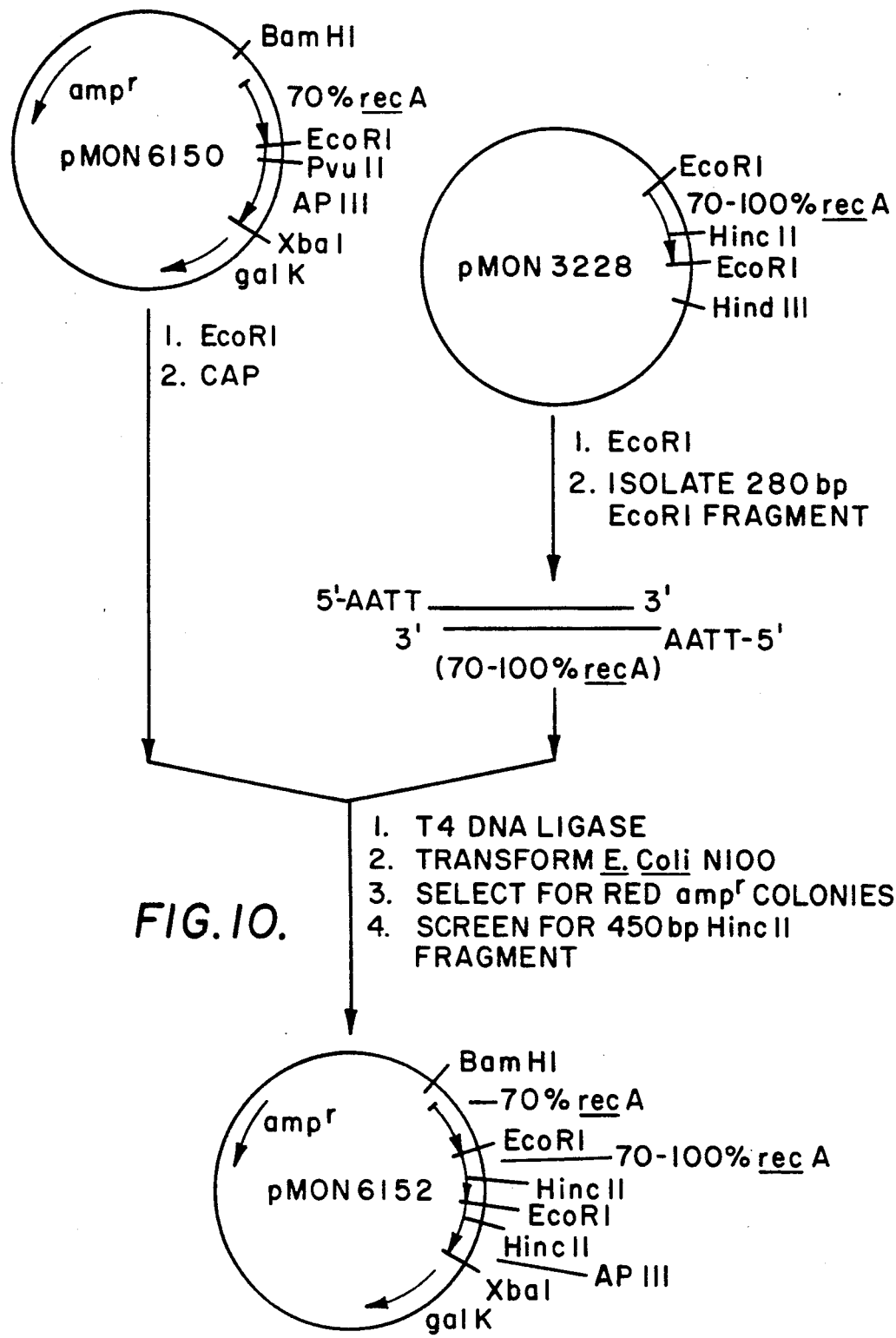
FIG. 10 depicts the construction of pMON6152 comprising a pMON6150 vector having inserted therein at the EcoRI restriction site a DNA sequence encoding 70-100% recA.

In an example of the present invention, expression vector pMON6152 comprising pKO1 carrying a complete recA gene and APIII DNA coding sequence was created as shown in FIGS. 7-10. A bacteria such as *E. coli* N100 was then stably transformed with the pMON6152 expression vector and transformants selected by growth on galactose MacConkey agar containing 200 μg/ml ampicillin as described more fully in the examples. The expression plasmids contained within the transformed bacteria were then screened for the presence of the recA and APIII coding sequences in the correct 5' to 3' orientation as shown in FIG. 10 by restriction enzyme cleavage.

Purification of the fusion protein produced will depend on both the protein and host cell chosen. Subsequent purification of the fusion protein to rid it of contaminating bacterial proteins can be achieved by conventional chromatographic means such as gel filtration, ion exchange chromatography or protein-specific (e.g. antibody or substrate) affinity chromatography. A detailed purification of recA-containing heterologous proteins (e.g. fusion proteins) employing a recA-specific monoclonal antibody described in a concurrently filed U.S. patent application by G.G. Krivi and M.L. Bittner entitled "Antibody Purification of recA Fusion Peptides" and having U.S. Ser. No. 747,126, incorporated by reference hereto. This concurrently filed U.S. patent application and the present application are commonly assigned to Monsanto Company. Additionally, the rec A protein and fragments thereof are highly negatively charged and as such are amenable to purification by such methods as anion exchange chromatography as described more fully in the examples below.

Fusion Protein Cleavage

Although some investigators have reported that V8 protease hydrolyzes only glutamoyl bonds in either ammonium bicarbonate (pH 7.8) or ammonium acetate (pH 4.0) buffer and hydrolyzes both aspartamoyl and glutamoyl bonds in phosphate buffer (pH 7.8) or sodium acetate buffer (pH 4.0), Houmard and Drapeau (1972a and b), other groups have found no difference in aspartamoyl and glutamoyl cleavage when either ammonium or phosphate buffers are employed. See Behrens and Brown (1976); Austen and Smith (1976). We have determined that the reduced form of a synthetic APIII when subjected to V8 protease digestion in ammonium bicarbonate buffer (pH 7.8) results in cleavage. Misono, D.S. et al. (1984) have reported cleavage of the aspartamoyl bond with V8 protease in sodium phosphate buffer (pH 7.8) in four distinct atrial peptides possessing both natriuretic activity and smooth muscle relaxant activity.

In a particularly preferred embodiment of the present invention, the purified oxidized fusion protein was subjected to V8 protease hydrolysis in an ammonium bicarbonate buffer (pH 7.8) as described more fully below. This buffer was chosen to potentially optimize site-specific cleavage at the junction glutamoyl bond. It has been found that by employing the methods of the present invention, one can achieve from about 80% to 90% release of the desired atrial peptide from the bacterially produced fusion protein.

As described more fully in the examples below, in the process of describing the novel release of atrial peptides from novel bacterially produced fusion proteins, we discovered that V8 protease preferentially cleaves a Glu-containing trigger signal present at the junction site thereby promoting early release of the desired peptide prior to cleavage of internal Glu residues present in the recA protein. We have furthermore discovered that fusion proteins comprising recA joined to an atrial peptide by a glutamic acid molecule promote an early release of a desired heterologous peptide as a single species when a recA-atrial peptide fusion protein is cleaved with V8 protease under appropriate reaction conditions as described more fully below.

Once the fusion proteins have been purified, the proteins are then subjected to endopeptidase cleavage to release the desired peptide. Alternatively, endopeptidase cleavage may be performed on crude extracts from bacteria producing the desired fusion protein and the desired peptide thereafter isolated and purified by conventional chromatographic means such as gel filtration, ion exchange chromatography or protein-specific (e.g. antibody or substrate) affinity chromatography.

In a particularly preferred embodiment of the present invention, the atrial peptide species produced and isolated as described above are shown to exhibit smooth muscle relaxant biological activity as assayed in accordance with methods described by Currie et al (1983) and set forth in U.S. Pat. No. 4,4986,544, the relevant portions of which are incorporated herein by reference.

Briefly, bioassays for the smooth muscle relaxant activity of the isolated peptide were made on rabbit aorta strips or on segments of chick rectum under physiologically acceptable conditions. See Currie et al (1983) and U.S. Pat. No. 4,496,544. Rabbit aorta strips maintained in tone by. a continuous infusion of norepinephrine provide a reliable and sensitive assay tissue for measuring the intensity and duration of relaxation by atrial peptides. Natriuretic activity of the isolated peptides may be determined by injecting intravenously in dogs and determining the effect on fractional sodium excretion in the urine. See White and Samson (1954); Pitts, R. F. (1974).

As previously discussed, the invention also contemplates the production and release of various atrial peptide species, variants thereof and other peptides produced as fusion proteins by bacteria. Such atrial peptide species and variants thereof having desirable natriuretic and/or smooth muscle relaxant activities can be identified by routine testing in the biological assays described above.

The following examples illustrate preferred embodiments of the present invention and are not intended to limit the invention's scope in any way. While this invention has been described in relation to its preferred embodiments, various modifications thereof will be apparent to one skilled in the art from reading this application.

Microorganisms, Plasmids and Materials

The following microorganisms have been deposited with the American Type Culture Collection (ATCC), 12301 Parklawn Drive, Rockville, Md., 20852, U.S.A.: ATCC 53147—*E. coli* JM101 (pDR1453).

This deposit is available to the public upon the grant of a U.S. patent. This deposit will be available for the life of any such U.S. patent having the benefit of the filing date of this application. However, it should be understood that the availability of a deposit does not constitute a license to practice the subject invention in derogation of patent rights granted by governmental action. Furthermore, the present invention is not to be limited in scope by the microorganism deposited, since the deposited embodiment is intended only as a specific illustration of the invention.

EXAMPLE 1

All oligonucleotides were synthesized in the Department of Biological Sciences, Monsanto Company, employing a 380A Applied Biosystems DNA synthesizer in accordance with the procedure set forth by the manufacturer, Applied Biosystems, Inc., Foster City, California. Restriction enzymes were purchased from New England Biolabs (Beverly, Mass.). *E. coli* DNA polymerase I, Klenow fragment (PolI), T4 DNA Kinase and T4 DNA ligase were purchased from New England Nuclear (Boston, Mass.) $^{32}$P-labeled nucleotides were purchased from Amersham (Arlington Heights, Ill.).

*E. coli* JM101 was obtained from Dr. J. Messing, University of Minnesota (St. Paul, Minn.) and may be obtained from the American Type Culture Collection (ATCC), Rockville, Md. under ATCC accession No. 33876. *E. coli* MM294 may be obtained from the ATCC under ATCC accession No. 33625. *E. coli* N100 may be obtained from the ATCC under ATCC accession No. 33965. GM48 was obtained from Dr. G. Marinus (University of Massachusetts Medical School, Worchester, Mass.).

Restriction enzyme digestions, the T4 DNA ligase reactions, and *E. coli* DNA polymerase I, Klenow fragment, reactions may be carried out in accordance with the procedures set forth by the manufacturers. Preferred buffers for the following restriction enzymes are as follows. For XbaI, BamHI, EcoRI, PstI, HincII, and HinfI: 50 mM NaCl, 6.6mM Tris-HCl, pH 8.0, 6.6 mM MgCl$_2$, 5 mM dithiothreitol (DTT). For SmaI: 20 mM KCl, 6 mM Tris-HCl, pH 8.0, 6 mM MgCl$_2$, 6 mM β-mercaptoethanol. T4 DNA ligase reactions were run in buffers containing 25mM Tris, pH 8.0, 10 mM MgCl$_2$, 10 mM dithiothritol (DTT), 2 mM spermidine and 0.2 mM ATP. *E. coli* DNA polymerase I, Klenow fragment, was used in a buffer containing 20 mM Tris, pH 7.2, 10 mM MgCl$_2$, 10 mM (DTT), 1 mM ATP, and 1 mM each dATP, dGTP, dCTP, dTTP, (dNTP's). The XbaI linker was obtained from Biolabs (Beverly, Mass.).

Alpha-$^{32}$P-dATP (400 Ci/mmol) was added to the Klenow reaction if labeling of the newly synthesized DNA strand was desired.

Oligonucleotides were labeled using gamma-$^{32}$P-ATP (sp. act. greater than 5000 Ci/mmol) and T4 DNA kinase in 100 mM Tris, pH 8.0, 10 mM MgCl$_2$, 5 mM DTT.

*Staphylococcus aureus* V8 protease was purchased from Miles Scientific (Naperville, Ill.). Factor Xa and thrombin were purchased from Boehringer Mannheim (Indianapolis, Ind.).

Vectors pK01, pUC18, pBR327, pBR322, M13mp8 and M13mp9 can be purchased from Pharmacia (Piscataway, N.J.). M13mp18 can be obtained from New England Biolabs (Beverly, Mass.). Additionally, pK01 and pBR322 can be obtained from the ATCC under ATCC accession Nos. 37126 and 37017, respectively. The M13mp9, M13mp8 and pUC18 vectors were obtained from Dr. J. Messing, University of Minnesota (St. Paul, Minn.). pUC9 and pUC8 can be obtained from Bethesda Research Laboratories, Inc. (Gaithersburg, Md.). Plasmid vector pK01 described in Chirikjian, J.G. and Papas T. (1981) was obtained from Dr. Martin Rosenberg (National Institutes of Health, Bethesda, Md.).

All bacterial growth media components and antibiotics were obtained from either Sigma (St. Louis, Mo.) or Difco Laboratories (Detroit, Mich.).

EXAMPLE 2

The following example describes the construction and assembly of the synthetic gene coding for the 24 amino acids of APIII, shown in FIG. 1. The coding portion of the sequence was preceded by a codon for glutamic acid to provide a recognition site for cleavage of APIII from a fusion protein with V8 protease. The coding portion of the sequence was preceded by a codon for glumatic acid to provide a recognition site for cleavage of APIII from a fusion protein with V8 protease. The coding portion of the sequence was immediately followed by tandem translation termination codons. Additionally, recognition sites for several restriction endonucleases were introduced into the polynucleotide sequence as shown in FIG. 1.

In order to produce the double-stranded DNA (dsDNA) fragment shown in FIG. 1, six complementary and partially overlapping synthetic oligonucleotides were synthesized as shown in FIG. 3. Aliquots of the crude synthetic oligonucleotides were purified by electrophoresis on polyacrylamide-urea gels, 16% (w/v) in 7M urea. See Sanger (1977). The concentration of the synthetic DNA in each preparation was determined by quantitative 5'-end labeling reactions using gamma-$^{32}$P-ATP at a specific activity of 22,000–24,000 counts per minute (cpm) per mole of ATP, and T4 DNA Kinase.

The oligonucleotides were then annealed by the following method. 50 picamoles (pmole) of each oligonucleotide was combined in a 25 microliter ($\mu$l) final volume reaction mix containing 25 mM Tris-HCl, pH 8.0, 10 mM MgCl$_2$, 10 mM dithiothreitol (DTT), and 0.2 mM spermidine, $\gamma$-$^{32}$P-ATP at 5000 cpm/pmole of DNA and 40 units of T4 DNA kinase. The reaction was incubated at 37° C. for 30 minutes and then placed in a boiling water bath for two minutes and then allowed to slowly cool to room temperature over a period of six hours. Four units of T4 DNA ligase and ATP (to 0.4 mM) were then added to the products of the annealing reaction and incubated at 4° C. for 16 hours to ligate said products. The ligation reaction was terminated by heating to 70° C. for 5 minutes.

The ligation products were then subjected to digestion with EcoRI restriction endonuclease to reduce the maximum size of the DNA fragments to monomers in the event the self-complementary EcoRI ends ligated to form polymers. The resulting DNA was purified by polyacrylamide gel electrophoresis (PAGE) on a 12% (w/v) gel, 10% (w/v) glycerol and a 93 bp molecular weight piece of DNA was electroeluted from the gel to yield the fragment, the complete DNA sequence of which is shown in FIG. 1.

EXAMPLE 3

The following example describes the construction and expression of two recombinant expression vectors which provide for the production in bacteria of fusion proteins having a V8 protease cleavage site at the junction site or bond. Specifically, one recombinant expression vector constructed contained a Glu coding sequence following the endogenous protein's DNA (i.e. recA) coding sequence and immediately preceding the coding sequence for the first amino acid (Ser) of the APIII peptide. This fusion construct is hereinafter referred to as recA-Glu-APIII. A second recombinant expression vector constructed contained a DNA sequence coding for Glu-Gly-Arg following the recA DNA coding sequence and immediately preceding the coding sequence for the first amino acid (Ser) of the APIII peptide. This fusion construct is hereinafter referred to as reca-Glu-Gly-Arg-APIII. The entire (100%) recA coding sequence was used in both gene constructs.

The Glu-Gly-Arg junction sequence provides two options for cleavage and subsequent release of a desired peptide, one using blood coagulation factor Xa and the second using V8 protease.

Thus, two distinct gene constructions were made, one coding for a recA-Glu-APIII fusion protein and the second coding for a recA-Glu-Gly-Arg-APIII fusion protein. Expression of the constructs was achieved by transforming an appropriate host cell and culturing the transformants under appropriate conditions as described more fully below.

a. Creation of a 70% recA-Containing Cloning Vector

The recombinant cloning vector pDR1461 comprising a modified pBR322 plasmid carrying the recA promoter and ribosome binding sequences and 70% of the recA DNA coding sequence, collectively referred to as 70% recA, in place of the tetracycline resistance (tet$^r$) gene was constructed as shown in FIG. 4.

Specifically, pDR1453 described by Sancar, A. et al. (1980) was isolated from E. coli JM101 transformed with pDR1453 by the methods set forth by Sancar, A. and Rupp, W. D. (1979). E. coli JM101 transformed with pDR1453 has been deposited with the ATCC in accordance with the provisions of the Budapest Treaty and has accordingly been assigned ATCC accession No. 53147.

pDR1453 carries the entire recA gene of E. coli. As shown in FIG. 4, 70% recA was excised from pDR1453 as an 1800 bp BamHI/EcoRI fragment and subsequently purified by agarose gel electrophoresis in 0.7% (w/v) agarose, see Maniatis et al. (1981), from which is was then electroeluted. Plasmid pBR322 was cleaved with BamHI and EcoRI and the small BamHI/EcoRI fragment carrying the tet$^r$ gene removed to create a linearized modified pBR322 plasmid. The latter was treated with calf intestine alkaline phosphatase (CAP) and then mixed with the 1800 bp 70% recA containing BamHI/EcoRI fragment in the presence of T4 DNA ligase as shown in FIG. 4. The mixture was then incubated overnight at 14° C. Insertion of the 70% recA fragment into the linearized modified pBR322 plasmid was initially ascertained by amp$^r$ colony formation. Insertion of the 70% recA was confirmed by cleavage of isolated recombinant plasmid, Maniatis et al. (1982), with BamHI and EcoRI which yields an 1800 bp fragment comprising the inserted sequence. The 1800 base pair fragment was identified by agarose gel electrophoresis in 0.7% (w/v) agarose as described by Maniatis et al. (1982). All subsequent restriction fragments were identified by this referenced method. The resultant recombinant cloning vector is referred to as pDR1461, shown in FIG. 4.

b. Creation of a 70-100% recA-Containing Cloning Vector

Recombinant cloning vector pMON3228 comprising a M13mp9 phage vector carrying the DNA coding sequences for the C-terminal 70% to 100% of recA was constructed as shown in FIGS. 5 and 6.

pDR1453 was isolated as described above and cleaved with PstI. As shown in FIG. 5, an 1800 bp PstI fragment containing a C-terinal portion of the recA coding sequence, as shown in FIG. 5, was then isolated and cleaved with HinfI. The sticky HinfI end was then converted to a blunt-end by mixing the digested HinfI fragments with E. coli polymerase I, Klenow fragment, herein referred to as PolI, and deoxynucleotide triphosphates (dNTP's) under appropriate reaction conditions, see e.g. Maniatis et al. (1982), and then cleaved with EcoRI. A 360 bp EcoRI/HinfI fragment containing the DNA coding sequence for 70-100% recA was then isolated by polyacrylamide gel electrophoresis. RF m13mp9 DNA, previously cleaved with EcoRI and SmaI and treated with CAP, was then mixed with the 70-100% recA fragment in the presence of T4 DNA ligase as shown in FIG. 5. The ligation mixture was incubated overnight at 14° C. Insertion of the 70-100% recA fragment into M13mp9 was initially ascertained by colorless plaque formation on a lawn of *E. coli* JM101, grown on 1×YT medium employing the soft agar overlay procedure described in Maniatis et al. (1982) which included 10 μl 100mM IPTG (isopropyl-β-D-thiogalactopyranoside) and 50 μl 2% (w/v) x-GAL (5-bromo-4-chloro-3-indolyl-β-D-galactopyranoside) in 3 ml of top agar, and transfected with said recombinant vector as described by Messing et al. (1983) and the ssDNA of the recombinant vectors isolated as described by Messing et al. (1982). Insertion of the 70-100% recA coding sequence was then confirmed by digestion of recombinant RF DNA with EcoRI and HindIII which yielded a 380 bp fragment as shown in FIG. 5. The resultant recombinant vector comprising M13mp9 carrying a DNA coding sequence for 70-100% recA was designated pMON2558.

Next, an EcoRI restriction site was introduced at the C-terminus of the recA coding sequence. Briefly, single-stranded DNA of pMON2558 was isolated as described by Messing et al. (1982) and was employed as a template in the oligonucleotide-directed site-specific mutagenesis essentially as described by Zoller and Smith (1982); Zoller and Smith (1983); Norris et al. (1983).

FIG. 6 diagrams the mutagenesis procedure for creation of an EcoRI restriction site at the C-terminus of the recA coding sequence. Specifically, the codon for recA amino acid residue number 352 was changed from one coding for aspartic acid (GAT) to one coding for phenylalanine (TTC). The mutagenesis was conducted as follows. An oligonucleotide primer shown in FIG. 6 containing the sequence of the desired mutation was used to prime synthesis of a closed-circular DNA copy of the ssDNA pMON2558 template. The closed-circular dsDNA molecules thus generated are separated from incomplete and ssDNA circles by alkaline sucrose gradient centrifugation as described by Zoller and Smith (1983). The closed-circular dsDNA molecules were then used to transform *E. coli* JM101 as described by Messing et al. (1982) and the resulting colorless plaques were lifted onto Pall filters obtained from Pall Ultrafine Filtration Corp. (Glen Cove, N.Y.) and screened for hybridization to a $^{32}$P-labeled form of the oligonucleotide primer used to generate the site-specific mutagenesis. The lifting of said plaques was conducted in accordance with methods described by the Pall Filter manufacturer. Hybridization screening was carried out using nylon Biodyne ® filters as described by Pall Ultrafine Filtration Corp. in their "Protocol Guide for DNA Transfer to Pall Biodyne™ A Nylon Filters" (1983). Filters were washed at increasing temperatures until the radiolabeled signal was removed from a control filter which was prepared with M13mp9/70-100% recA phage. A typical filter washing protocol employed a room temperature wash in 6xSSC (0.9M NaCl and 0.09M NaCitrate) for 10 minutes (min.) followed by a 50° C. wash in 6xSSC for 5 min. and subsequent washings at temperatures increasing by 5° C. Plaques which hybridized to radiolabeled oligonucleotide primer at temperatures higher than the control phage were presumed to carry the newly created 70-100% recA with C-terminal EcoRI site coding sequence and were termed potential positives. Alternatively, individual colorless plaques were picked from the *E. coli* JM101 transformations and grown in 5 milliliters (ml) of 2×YT medium [1.6% (w/v) tryptone, 1.0% (w/v) yeast extract, 0.5% (w/v) NaCl] overnight at 37° C. with aeration. Phage DNA, prepared in accordance with Messing et al. (1982), was then spotted onto nitrocellulose, hybridized with radiolabeled primer, and washed in increasing temperatures as described above. Phage DNA which showed hybridization temperatures higher than M13mp9/70-100% recA control plaques were similarly termed potential positives. Potential positive plaques from both screening procedures were grown as described above and used to prepare ss phage DNA, which was then sequenced according to the procedure of Sanger et al. (1977) to confirm that they carried the coding sequence for 70-100% recA with the pMON3228. The frequency of addition of the EcoRI site adjacent the C-terminal amino acid codon for recA was about 2-5%.

Figure 7:
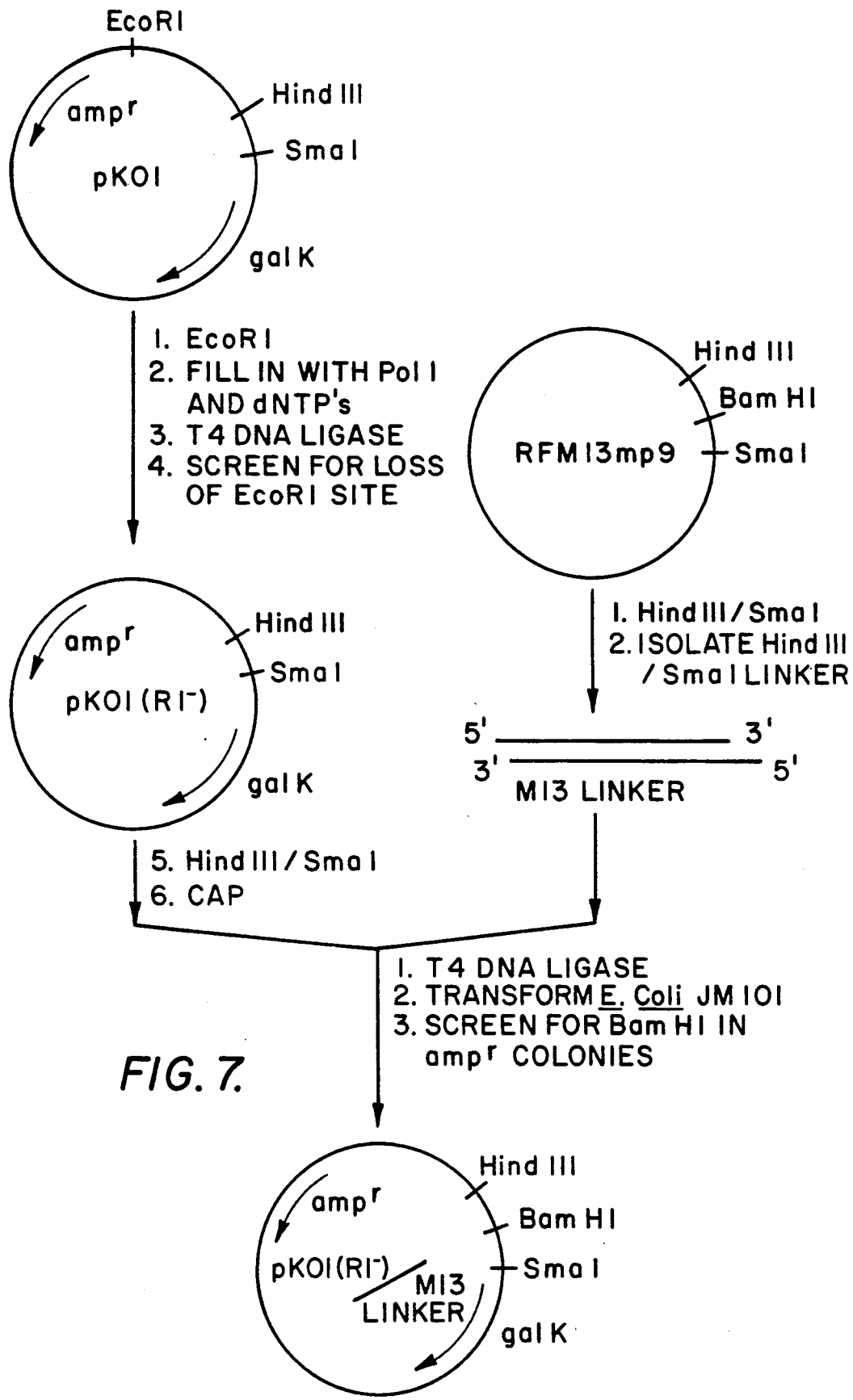
FIG. 7 depicts the construction of pK01(RI⁻)/M13 linker comprising a pK01 vector in which the EcoRI restriction site has been removed and having inserted therein at the HindIII/SmaI restriction site a M13mp9 linker carrying a BamHI restriction site.

C. Creation of a recA-Glu-APIII Expression Vector pMON6152, an expression vector capable of producing a recA-Glu-APIII fusion protein in a transformed *E. coli* host under appropriate conditions was constructed as shown in FIGS. 7-10. Briefly, a modified pK01 plasmid vector [pK01(RI$^-$)] was constructed as shown in FIG. 7. pK01(RI$^-$) comprises a pK01 plasmid in which the unique EcoRI restriction site has been removed by digesting pK01 with EcoRI, converting the sticky-ends to blunt-ends by filling in the ends as previously described, and incubating the blunt-ended linearized plasmid with T4 DNA ligase overnight at 14° C. *E. coli* JM101 were then transformed with pK01(RI$^-$) as described by Maniatis et al. (1982) and the pK01(RI$^-$) isolated as described in Chirikjian, J. and Papas, T. (1981). The absence of an EcoRI site in pK01(RI$^-$) was confirmed by demonstrating the vector's resistance to EcoRI cleavage.

pK01(RI$^-$) was then cleaved with HindIII and SmaI and the small HindIII/SmaI fragment removed. The linearized pK01(RI$^-$) with its HindIII/SmaI fragment deleted was then treated with CAP. The linearized plasmid contains no BamHI restriction sites. RF M13mp9 DNA, isolated as previously described, was cleaved with Hind III and SmaI. The small HindIII/SmaI fragment, herein referred to as the M13 linker, carrying an internal BamHI site was isolated by acrylamide gel electrophoresis. The M13 linker was inserted into the linearized pK01(RI$^-$), as shown in FIG. 7, by mixing the linker with the linearized plasmid in the presence of T4 DNA ligase and incubating overnight at 14° C. *E. coli* JM101 were then transformed with the ligation mixture as described by Maniatis et al. (1982).

Insertion of the M13mp9 linker into pK01(RI$^-$) was initially confirmed by growth of amp$^r$ colonies on Luria Bertani (LB) plates containing 200 μg/ml ampicillin. Insertion of the linker into the plasmid vector was confirmed by isolating the pK01(RI$^-$)/M13 linker vector as previously described and cleaving with BamHI to demonstrate the introduction of a BamHI site.

Next, the SmaI site in the pK01(RI$^-$)/M13 linker vector was converted to an XbaI site as shown in FIG. 8. Briefly, the pK01(RI$^-$)/M13 linker vector was cleaved with SmaI, treated with CAP, heat inactivated, and then mixed with a synthetic XbaI linker in the presence of T4 DNA ligase as previously described. *E. coli* JM101 were then transformed with the litigation mixture as previously described. Insertion of the XbaI site was screened for isolating the plasmids from amp$^r$ colonies and demonstrating successful cleavage thereof with XbaI. The resultant plasmid was referred to as pK01(RI−)/XbaI as shown in FIG. 8.

Next, the APIII and 70% recA DNA coding sequences were inserted into pK01(RI−)/XbaI at its BamHI site to create recombinant vector pMON6150 as shown in FIG. 9. Briefly, pK01(RI−) was cleaved with BamHI and XbaI and the small BamHI/XbaI fragment removed as previously described. The linearized pK01(RI−)/XbaI vector was then mixed, in the presence of T4 DNA ligase, with the 87bp EcoRI/XbaI fragment containing the APIII DNA coding sequence and 1800 bp BamHI/EcoRI fragment containing the 70% recA DNA coding sequence which fragments were isolated as shown in FIG. 9. Creation of the pMON6150 vector containing the DNA encoding 70% recA fused to DNA encoding APIII was verified by screening plasmids isolated from red amp$^r$ colonies on galactose MacConkey agar plates containing 200 μg/ml ampicillin transformed with the ligation mixture for the presence of an 1800 bp BamHI/EcoRI fragment and an 1800 bp BamHI/PvuII fragment as shown in FIG. 9.

Expression vector pMON6152, carrying the complete gene for expression of the recA-Glu-APIII fusion protein, was constructed as shown in FIG. 10. Briefly, the 280 bp EcoRI fragment containing DNA encoding 70-100% recA was isolated from pMON3228 as shown in FIG. 10 and inserted into the EcoRI site on pMON6150 as shown in FIG. 10. The proper 5' to 3' orientation of the 70-100% recA DNA coding sequence with respect to the APIII and 70% recA DNA coding sequences was confirmed by demonstrating the presence of a 450bp HincII fragment. Improper orientation of the 70-100% recA DNA coding sequence would have resulted in the generation of a 525 bp HincII fragment upon cleavage of the newly created recombinant expression vector with HincII.

D. Construction of the recA-Glu-Gly-Arg-APIII Expression Vector

A recA-Glu-Gly-Arg-APIII DNA coding sequence was created by inserting, sequentially, codons for the amino acids glycine (Gly) and arginine (Arg) immediately preceding the N-terminal serine codon of APIII using the techniques of oligonucleotide-directed site-specific mutagenesis previously described. Briefly, pMON6152 transformed into a dam$^−$ host (e.g. a host not expressing a DNA A methylase gene product) was cleaved with BamHI and XbaI and the 2200 bp BamHI/XbaI fragment carrying the recA-Glu-APIII fusion gene isolated and inserted into the BamHI to XbaI site in the cloning vector pUC18 as shown in FIG. 11 to create pMON6154. The dam$^−$ host employed was GM48.

The BamHI/HindIII fragment, shown in FIG. 11, carrying the recA-Glu-APIII fusion gene was then isolated from pMON6154 and cloned into the BamHI site in M13mp8 and single-stranded recombinant M13mp8 DNA carrying the recA-Glu-APIII gene isolated. An oligonucleotide primer comprising the anticoding sequence 5'-GAACAGCTGGAACGCCCTT-CGAATTCGTT-3' which contained the sequence of the desired mutation (i.e. addition of Gly and Arg codons), immediately preceding the N-terminal serine codon of APIII was then used to prime synthesis of a closed-circular DNA copy of the single-stranded recombinant M13mp8 DNA vector as previously described. Phage DNA carrying the desired Gly-Arg insertion to create a DNA sequence encoding the recA-Glu-Gly-Arg-APIII gene were identified in accordance with the methods previously described. The presence of a DNA sequence encoding a recA-Glu-Gly-Arg-APIII gene was confirmed by DNA sequencing. Positive isolates were then replicated in *E. coli* JM101, RF recombinant M13Mp8 DNA was then isolated and cleaved with BamHI and HindIII to yield a BamHI/HindIII fragment carrying the recA-Glu-Gly-Arg-APIII gene. The BamHI/HindIII fragment was then inserted into a pBR327 expression vector previously cleaved with BamHI and HindIII to create expression vector pMON6159.

Expression of recA-Glu-APIII and recA-Glu-Gly-Arg-APIII

*E. coli* JM101 were then transformed with either pMON6152 or pMON6159 employing the CaCl$_2$ method described by Maniatis et al. (1982) and then induced as follows. Single colonies of *E. coli* JM101 carrying either pMON6152 or pMON6159 were inoculated separately and grown overnight at 30° C. with aeration. One milliliter (ml) of the overnight cultures was then used to separately inoculate 15 ml of M9 media described by Miller, J.H. (1972) supplemented with 1% (w/v) glucose and 0.5% (w/v) casamino acids and grown at 30° C. to a density of 150 Klett units. The cells were then induced by adding nalidixic acid to a final concentration of 50 μg/ml and then incubated for 4 hours at 37° C. Prior to harvesting the cells, an aliquot of 10 Klett mls was then removed from each induced culture and individually lyse in sodium dodecyl sulfate (SDS)-polyacrylamide gel electrophoresis buffer and analyzed by SDS-PAGE in accordance with Laemmli (1970). Proteins of 41,000 daltons comprising recA-APIII fusion proteins were at high levels in *E. coli* JM101 from both of the two gene constructs. *E. coli* JM101 carrying parental pBR327 and pK01 plasmids do not produce a protein of 41,000 daltons. The induced transformed cells were then harvested by pelleting and stored at −70° C. as a frozen pellet.

EXAMPLE 4

This example demonstrates the cleavage of the Glu-Ser and Glu-Gly-Arg trigger signals by V8 protease. In this example, the bacterially produced fusion proteins were first isolated from substantially all (about 80-85%) host proteins by immunoaffinity or anion exchange chromatogrphy, subjected to V8 protease cleavage and thereafter the desired peptide, APIII, was purified.

A. Isolation of recA Fusion Proteins

Both the recA-Glu-APIII and recA-Glu-Gly-Arg-APIII fusion proteins bind to an anion exchange resin such as Fractogel ®TSK DEAE-650m at pH 7.0 to 9.0 and are eluted therefrom by 100-300 mM NaCl depending upon the pH. The Fractogel ®TSK DEAE-650m, hereinafter DEAE TSK, anion exchange resin obtained from E.M. Science (Gibbstown, N.J.) was prepared as follows. A 500 ml DEAE TSK column was prepared and equilibrated with a buffer comprising 100 mM NaCl and 50 mM Tris-HCl, pH 7.5. A 25 gram quantity of cell paste, isolated as described above, was resuspended in 250 mls of 50 mM Tris-HCl, pH 7.5, at 8° C. The cell suspension was sonicated using a Heat Systems-Ultrasonic, Inc. (Farmingdale, N.Y.), Model 10-375, containing a ¾ inch tip, for a total of 6 minutes in 1 minute increments at a maintained temperature ranging from about 8° C. to about 18° C. The sonicated suspension was then centrifuged at 26,000 xg. for 20 minutes. The supernatant containing about 5 to about 7 grams of protein was decanted from the solid pellet and applied to the surface of the anion exchange column at 8° C. at a flow rate of about 5 ml per minute. A linear gradient of increasing NaCl concentration ranging from about 100 mM NaCl to about 350 mM NaCl was applied to the column and fractions containing about 25 ml each collected, and was shown to resolve the fusion proteins from about 80% of all *E. coli* proteins. Elution of proteins from the column was monitored by ultraviolet absorbance at 280 mM and by electrophoretic analysis. Those fractions containing fusion protein were combined. The fusion proteins elute at about 280 mM NaCl which is substantially higher than that required to elute most *E. coli* proteins. Alternatively, $NH_4Cl$ was employed to resolve the fusion proteins from *E. coli* proteins. A linear gradient of increasing $NH_4Cl$ concentration ranging from about 100 mM $NH_4Cl$ to about 350 mM $NH_4Cl$ was applied to the column as described for NaCl from about 80-85% of all *E. coli* proteins. The fusion proteins elute at about 200 mM to about 230 mM $NH_4Cl$.

The recA monoclonal antibody described in a concurrently filed U.S. patent application Ser. No. 747,136 by G.G. Krivi and M.L. Bittner entitled "Purification of recA Fusion Peptides" and commonly assigned to Monsanto Company was also successfully applied to yield highly purified recA-Glu-APIII fusion proteins.

B. V8 protease Cleavage

The fusion protein pool from the DEAE TSK or recA monoclonal antibody columns comprising either the recA-Glu-APIII or recA-Glu-Gly-Arg-APIII fusion protein was dialyzed against 50 mM $NH_4HCO_3$. Briefly, approximately 800 to 1000 mls of column eluate containing the fusion protein was dialyzed against 24 liters of 50 mM $NH_4HCO_3$, pH 7.7 to 8.3, for 6 hours (hrs.) at 4° C. and thereafter centrifuged at 12,000 to 15,000 xg for 10 min. at 4° C.

Approximately 0.3 to 1.0 mg per ml fusion protein was mixed with V8 protease at a molar enzyme to substrate ratio ranging from 1:20 to 1:1000 in 50 mM $NH_4HCO_3$, pH 8.0, and incubated at 37° C. A typical cleavage reaction using a 1:500 molar enzyme to substrate ratio was stopped after 4 hours incubation by freezing or by addition of an anion exchange resin which binds the protease as described more fully below.

Approximately 80% of the APIII contained within the recA-Glu-APIII fusion protein and about 50% of the APIII contained within the recA-Glu-Gly-Arg-APIII fusion protein was found to be released as determined by the chick rectum relaxation assay, previously described, and/or by HPLC analysis. Briefly, APIII was resolved from other cleavage reaction peptides on a reverse phase analytical HPLC column containing Vydac ™ silica, 18 carbon chain derivatized (5 micron bead size) obtained from the Separations Group (Hesperia, Calif.) using a Waters Associates (Milford, Mass.) System. The reverse phase column was equilibrated with 10% (v/v) acetonitrile and 0.5% (v/v) trifluoroacetic acid (TFA) at a flow rate of about 1 ml per minute. Following application of the cleavage products to the column, a gradient of increasing acetonitrile ranging from about 10% (v/v) to about 50% (v/v) acetonitrile and 0.05% (v/v) TFA was applied to resolve the peptides. The column was then washed with a gradient of increasing acetonitrile up to 100% (v/v) acetonitrile plus 0.05% (v/v) TFA. APIII eluted from the reverse phase column was quantitated by comparing the area under the peaks to a commercial APIII standard obtained from Peninsula Laboratories (San Carlos, Calif.).

The cleavage reaction mixture was then lyophilized to remove any acetonitrile or $NH_4HCO_3$ and then resolubilized in 10% (v/v) acetonitrile and 0.05% (v/v) TFA prior to APIII purification. Any insoluble species which may have formed during the cleavage reaction were removed by centrifugation at about 12,000 to about 15,000 xg for 10 minutes at 4° C.

C. APIII Purification

The majority of the recA fragments and V8 protease were removed by mixing the cleavage reaction mixture with an anion exchange resin such as DE52 cellulose obtained from Whatman, Limited (Great Britain). The DE52 resin was equilibrated with 50 mM $NH_4HCO_3$, pH 8.0, in accordance with manufacturers' instructions at room temperature. Approximately 1 ml of resin was employed for every 2.5 mg of fusion protein and the mixing of resin and cleavage reaction mixture is maintained by stirring for 1 hr. at room temperature. APIII does not bind to the resin and was removed from the resin-containing mixture by filtering the mixture through Whatman No. 1 filter paper obtained from Whatman, Limited (Great Britain) followed by filtration through a 0.45 micron filter unit, such as a Type LS obtained from Nalge Co. (Rochester, N.Y.).

The APIII peptide was further purified on a low pressure reverse phase chromatography system. Briefly, a 50 ml column of medium bead size silica such as Vydac ™, 15-20 microns, derivatized with 18 carbon chains (C-18) obtained from the Separations Group (Hesperia, Calif.) was employed. The pH of the sample was adjusted to pH 2.5 with TFA and the sample degassed before application to the column. A gradient system of acetonitrile with 0.5% (v/v) TFA, comprising from about 5.0% (v/v) acetonitrile to about 20% (v/v) acetonitrile in 0.2% (v/v) per minute increments was used to resolve the contaminant peptides from APIII. APIII eluted at about 15% (v/v) acetonitrile and the resultant APIII peptide was about 80% free from other proteins or protein fragments. HPLC, as described below, was then employed to further purify the low pressure reverse phase APIII product.

Alternatively, HPLC was employed to purify about 0.5 mg APIII directly from the V8 protease cleavage reaction using the Waters Associates (Milford, Mass.) reverse phase system described above with the following modifications. A gradient of acetonitrile ranging from about 10% (v/v) to about 40% (v/v) and containing 0.05% (v/v) TFA was applied in 1.0 to 2.0% (v/v) per minute increments at a flow rate of about 2 to 4 ml per minute. APIII was found to elute at approximately 30% (v/v) acetonitrile and 0.05% (v/v) TFA.

A single APIII peak was resolved by HPLC from the recA-Glu-APIII V8 protease cleavage reaction; the peak containing 80% of the total APIII obtainable from the fusion protein. Three peaks were resolved by HPLC from the recA-Glu-Gly-Arg-APIII V8 protease cleavage reaction containing approximately 50% of the total APIII obtainable from the fusion protein. Cleavage of both the recA-Glu-APIII and recA-Glu-Gly-Arg-APIII fusion proteins with V8 protease resulted in the endogenous protein remaining substantially intact such that the released APIII peptide was clearly resolved from any fragments generated in the cleavage reaction.

N-terminal amino acid sequencing of the peak peptides was performed using an Applied Biosystems Protein Sequencer Model 470A (Applied Biosystems, Inc., Foster City, Calif.) in accordance with the method described by Hunkapillar et al. (1983a) and Hunkapillar et al. (1983b).

Table I, below, shows the results of the sequence analysis for both the recA-Glu-APIII and recA-Glu-Gly-Arg-APIII V8 protease digests. The last, C-terminal, 10 amino acids of the recA protein comprising the sequence . . . ser-glu-gly-val-ala-glu-thr-asn-glu-phe-COOH, contains three potential (Glu) V8 protease cleavage sites. Additionally, the recA protein contains numerous internal glutamic acid (glu) residues which may be actively cleaved by V8 protease. As shown by the N-terminal sequencing results presented in Table I, below, no evidence for V8 protease cleavage within the 10 C-terminal recA amino acid sequence is seen prior to the release of 80% of the APIII contained within the recA-Glu-APIII fusion protein. Conversely, all three glu residues within the 10 C-terminal amino acids of recA trigger V8 protease cleavage to an almost equivalent extent of V8 protease cleavage at the junction site trigger signal (Glu-Gly-Arg).

These results demonstrate that cleavage of these fusion proteins with V8 protease resulted in a preferred cleavage of the trigger signal at the junction site while the trigger signals within the endogenous protein remained substantially intact thereby providing a clear resolution of the desired heterologous peptide (i.e. APIII). These results further demonstrate a most preferred cleavage of a junction site Glu contained within a recA-Glu-atrial peptide fusion protein. As shown in Table I, below, fusion proteins having a junction site comprising Glu-Gly-Arg resulted in cleavage at both the junction site glutamic acid bond and at internal recA glutamic acid bonds.

The biological activity of the HPLC purified APIII peptides obtained by V8 protease cleavage of both the recA-Glu-APIII and recA-Glu-Gly-Arg-APIII fusion proteins was confirmed as previously described.

TABLE I

N-terminal sequence analysis of recA—Glu—APIII and recA—Glu—Gly—Arg—APIII fusion proteins cleaved with V8 protease.

| Sample | I N-Terminal amino acids | II % of APIII[1] |
|---|---|---|
| recA—Glu—APIII | Ser—Ser | 100% |
| recA—Glu—Gly—Arg—APIII | Gly—Val | 5 |
|  | Thr—Asn | 15 |
|  | Phe—Glu | 40 |
|  | Gly—Arg | 40 |

[1]The amount of peptide with the N-terminal sequence shown in column I is shown as a percent (%) of the total APIII in the sample.

EXAMPLE 5

This example demonstrates the cleavage at a Phe-Glu-Gly-Arg trigger signal with factor Xa. This trigger signal represents a novel factor Xa recognition site effective for the site-specific release of atrial peptides from recA-atrial peptide fusion proteins. In this example, the fusion protein was first isolated by anion exchange chromatography, subjected to factor Xa cleavage and then the desired peptide, APIII, was purified.

A Isolation of RecA Fusion

The recA-Glu-Gly-Arg-APIII fusion was purified by anion exchange chromatography as described in Example 4. The fusion protein eluted at about 200 mM to about 230 mM NH$_4$Cl.

B. Factor Xa Cleavage

The fusion protein pool at a protein concentration of approximately 0.3 mg/ml was mixed with factor Xa (Boehringer Mannheim; Indianapolis, Ind.) at a molar enzyme to substrate ratio ranging from about 1:20 to about 1:100 in buffer comprising 50 mM Tris-HCl, pH 7.5, and 200–230 mM NH$_4$Cl. Calcium chloride at a final concentration of 5 mM–50 mM and approximately 20 $\mu$M (final concentration) phospholipid vesicles were added to enhance the rate of cleavage. The vesicles were prepared with Folch fraction III (Sigma Chemical; St. Louis, Mo.) and phosphatidyl inositol at a ratio of 90:1. The crude lipids were extracted with acetone then a 2:1 molar ratio of chloroform:methanol was used to solubilize the phospholipid and the resultant solution was dried under a stream of nitrogen gas. The phospholipid was washed twice with ether to remove residual chloroform. Buffer comprising 50 mM Tris-Cl, pH 8.0, was added to the phospholipid to yield a final 25 mM phosphate concentration. The solution was then sonicated in an ice bath until clear. The cleavage reaction was incubated at 25° C. for 4–20 hours and stopped by freezing or by immediately purifying the product peptide.

C. APIII Purification

The recA fragment and factor Xa were removed and the APIII purified to homogeneity by reverse phase HPLC as described above.

Approximately 80% of the APIII contained within the fusion was released as determined by chick rectum relaxation activity and analytical reverse phase HPLC peak areas as described in Example 4. Few if any other peptide-like fragments other than APIII were specifically released from the fusion with no other major cleavage occurring in the fusion.

The biological activity of the HPLC purified APIII peptides obtained by factor Xa cleavage of the fusion proteins was confirmed as previously described.

EXAMPLE 6

This example demonstrates the expression and cleavage of fusion proteins containing a Glu-Ser trigger signal present at the junction site between either 100% recA and API or bacteria 100% recA and APIV.

A. Creation of Expression Vectors

A recA-Glu-API DNA coding sequence was created by using the technique of oligonucleotide-directed site-specific mutagenesis as previously described. Specifically, the codons for amino acids 22 through 24 (Phe, Arg, Tyr) were removed from the Glu-APIII gene, to create Glu-API. To accomplish this, the M13mp9/APIII ssDNA, shown in FIG. 2, was employed as a template for oligonucleotide-directed site-specific mutagenesis. An oligonucleotide primer comprising the coding sequence 5'-TTGGGTGTAACTCTTTAATGATCTAGAGA-3' which contained the sequence of the desired mutation (e.g. deletion of the Phe, Arg, Tyr codons, immediately preceding the termination codons) was then used to prime synthesis of a closed-circular DNA copy of the single-stranded recombinant M13mp9 DNA. The presence of a DNA sequence encoding the Glu-API gene was confirmed by DNA sequencing. Positive mutant phage were then replicated in *E. coli* JM 101 strain and double-stranded replicative form (RF) M13mp9 mutant DNA was then isolated and cleaved with EcoRI to yield an EcoRI fragment carrying the Glu-API gene. The EcoRI fragment was then inserted into pMON6075, a pUC9 expression vector, previously cleaved with EcoRI and carrying the recA gene on a BamHI/EcoRI fragment, obtained from pMON6152. Clones isolated from this transformation were screened by cleaving with the restriction enzymes EcoRI and ClaI independently to determine the presence and orientation of the API gene. A positive clone created the expression vector pMON6163 comprising recA-Glu-API.

A recA-Glu-APIV DNA coding sequence was created by inserting a synthetic DNA fragment into the EcoRI/PvuII restriction sites of the APIII gene (See FIG. I). The synthetic DNA fragment contained the codons for the amino acids Glu-Ser-Leu-Arg-Arg to be inserted immediately preceding the N-terminal serine codon of APIII. The coding sequence of the synthetic DNA was as follows:

```
5'-AA TTC GAA TCC CTG CGC CGT TCC AG-3'
   Glu—Phe—Glu—Ser—Leu—Arg—Arg—Ser—Ser
```

The expression vector pMON6159 was cleaved with EcoRI and PvuII and the large linear fragment ligated to the synthetic DNA fragment and transformed into *E. coli* JM101 as previously described. The recA-Xa-APIII DNA coding sequence was thereby changed to comprise a recA-Glu-APIV DNA coding sequence. Clones isolated by this procedure were screened by restriction analysis cleaving with EcoRI/HindIII to yield a 124 b.p. fragment. Additionally, the DNA coding sequence was confirmed by DNA sequencing. Specifically, the gene of a positive clone was transferred on a BamHI/HindIII fragment to M13mp18 phage RF DNA that had previously been cleaved with BamHI/HindIII. Single-stranded DNA was prepared from colorless plaque obtained in this transformation and served as the template for dideoxy sequencing (Sanger et. al., 1977). A positive clone, that was verified by DNA sequencing, created the expression vector comprising pBR327 containing recA-Glu-APIV, and was designated pMON6164.

B. Expression, Purification and Cleavage of recA-Glu-API and recA-Glu-APIV

*E coli* JM101 were transformed with either pMON6163 or pMON6164 as previously described above. The transformed cells were then induced by adding nalidixic acid to the culture medium as previously described. The high level production (i.e. 10–30% of the total host protein) of fusion proteins comprising recA-Glu-API or recA-Glu-APIV was confirmed as previously described.

Both the 100% recA-Glu-API and 100% recA-Glu-APIV fusion proteins were produced as aggregates contained in inclusion (i.e. refractile) bodies. Examples of methods for purifying such proteins from bacteria are described in U.S. Pat. Nos. 4,511,502 and 4,511,503. In the present example, one gram of cell paste was resuspended in 20 mls of distilled, deionized water at 8° C. The cell suspension was sonicated using a Heat Systems-Ultrasonic, Inc. (Farmingdale, N.Y.), Model 10-375, containing a ½ inch tip, for a total of 3 minutes in 1 minute increments. Temperature was maintained at 8°–15° C. The sonicated suspension was then centrifuged at 5000 xg. for 10 minutes. The supernatant was discarded.

The recA-Glu-APIV solid pellet was resuspended in 20 mls 50 mM sodium acetate, pH 5.5, at 8° C. This resuspension in 50 mM sodium acetate and subsequent pelleting at 7500×g. was repeated 3 times. The final pellet was then dissolved in 5 mls 9.0M urea, 50 mM Tris-HCl, pH 7.5, at 8° C. and then centrifuged at 10,000 xg. to remove any remaining cellular debris. The supernatant was then diluted to a final concentration of 2.0M urea with 50mM Tris-HCl, pH 7.9 and subjected to immunoaffinity chromatography as described below.

A 10 ml recA monoclonal antibody affinity column described in a concurrently filed U.S. patent application having U.S. Ser. No. 747,136 incorporated by reference hereto was equilibrated with 25 mM Tris-HCl, 150 mM NaCl, pH 7.9, at 8° C. The suspension containing the fusion protein was applied to the surface of the column at 8° C. at a flow rate of approximately 1 ml per minute. The flow rate was maintained at 1 ml per minute for the entire procedure. Fractions containing about 2 ml were collected. The column eluate was monitored by ultraviolet absorbance at 280 nm and electrophoretic analysis. The column, with the fusion protein bound, was washed with 20–50 ml of 25 mM Tris-Cl, 500 mM NaCl, pH 7.9, at 8° C. The column was then washed with 25 mM Tris-Cl, 150 mM NaCl, pH 7.9, at 8° C. The fusion protein was eluted with 200 mM glycine, 150 mM NaCl, pH 2.5, at 8° C. Fractions collected at this point were neutralized with 100 microliters of 1 M Tris.

The 100% recA-Glu-APIV fusion (0.5 ml) after urea solubilization and immunoaffinity chromatography was dialyzed versus three changes of 300 ml of 50 mM NH4HCO3 for 20 hours at 4° C. The 100% recA-Glu-API solid pellet was directly solubiled in 7M urea, 50 mM Tris-HCl pH 7.5, and then was dialyzed versus two changes of 50 mM NH4HCO3, pH8.0 for 20 hours, at 4° C.

After dialysis the fusions were diluted to about 0.5 mg/ml protein. The fusions were incubated with a 1 to 500 molar ratio enzyme to substrate of V8 protease. The incubations were for 4 hours at 37° C. and the reactions were stopped by freezing.

The fusion cleavage mixtures were analyzed on a Waters Associates HPLC reverse phase system as described previously. The column was equilibrated with 10% (v/v) acetonitrile and 0.05% trifluoroacetic acid (v/v). After applying the sample, a linear gradient of 10% to 50% acetonitrile (v/v) with 0.05% trifluoroacetic acid (v/v) in 1% per minute increments at a flow rate of 1 ml per minute was used to separate the API or APIV from the recA fragments. Quantitation was done by comparing the HPLC areas of the API or APIV released from the fusions with commercial API and APIV from Peninsula Laboratories (San Carlos, Calif.). Approximately 80% of the theoretical API and APIV in the fusion was released within 4 hours.

C. API and APIV Purification

The cleaved fusion mixes were dried and reconstituted with 10% (v/v) acetonitrile with 0.05% (v/v) trifluoroacetic acid. The API and APIV were resolved from contaminating proteins on a semipreparative 10×250 mm 5 micron C-18 Vydac column (Separations Group, Hesperia, Calif.). The chromatography conditions were the same as for the analytical chromatography except the flow rates were increased to 2 ml per minute. The peak with API or APIV retention time was collected as it eluted from the column.

Both the API and APIV were bioactive in the chick rectum relaxation assay. Both API and APIV were amino acid sequenced as described above.

EXAMPLE 7

This example demonstrates the construction of expression vectors comprising a pBR327 plasmid having inserted therein a gene encoding a fusion protein comprising 100% recA, a thrombin cleavage site and atrial peptide APIII or APIV.

The thrombin cleavage site or trigger signal comprised either the amino acid sequence: NH2-Arg-Ala-Leu-Leu-Ala-Gly-Pro-Arg-COOH or NH2-Gly-Pro-Arg-COOH. The former thrombin trigger signal is hereinafter referred to the "extended thrombin site" and the latter is referred to as the "truncated thrombin site."

An expression vector containing a gene coding for a fusion protein comprising 100% recA, an extended thrombin site and APIV was constructed as follows. A double-stranded (ds) DNA fragment coding for the extended thrombin cleavage site and the first three amino-terminal amino acids of APIV was chemically synthesized in accordance with procedures described above. The coding strand of the synthetic DNA fragment comprised the sequence:

```
5'-AA TTC GGT GCT CTC CTG GCT GGC CCG CGT
    Glu—Phe—Arg—Ala—Leu—Leu—Ala—Gly—Pro—Arg—

TCC CTG CGC CGT TCC AG-3'
Ser—Leu—Arg—Arg—Ser—Ser
```

The synthetic ds DNA fragment was then inserted into pMON6159 previously cleaved with EcoRI and PvuII. The factor Xa (Glu-Gly-Arg) and APIII coding sequences contained within pMON6159 were thereby converted to DNA sequences coding for an extended thrombin cleavage site and APIV yielding a novel expression vector designated pMON6160. The creation of pMON6160 was confirmed by restriction endonuclease cleavage analysis and DNA sequencing as previously described.

An expression vector comprising a pBR327 plasmid containing a gene for a fusion protein comprising 100% recA, a truncated thrombin trigger signal and APIII was constructed as follows. In accordance with procedures previously described, a synthetic DNA fragment was chemically synthesized which fragment contained the following coding sequence:

```
5'-AA TTC GGG CCG CGT TCC AG-3'
    Glu—Phe—Gly—Pro—Arg—Ser—Ser
```

The synthetic DNA fragment was then inserted into pMON6159 in place of the EcoRI/PvuII restriction fragment of pMON6159. The creation of an expression vector, designated pMON6166, containing a gene for a fusion protein comprising 100% recA-Gly-Pro-Arg-APIII was confirmed by restriction endonuclease cleavage and DNA sequencing as previously described.

EXAMPLE 8

This example demonstrates the expression in bacteria of fusion proteins comprising 100% recA, a thrombin trigger signal and APIII or APIV and the purification of APIII or APIV therefrom.

E. coli JM101 cells were transformed with either pMON6160 or pMON6166 and subsequently induced by addition of nalidixic acid to the culture media, all as previously described.

The fusion proteins were then purified as previously described for 100% recA-Glu-APIV.

Approximately 2 to 5 milliliters (ml) of purified fusion protein was dialyzed in one liter of buffer comprising 50 mM Tris-HCl, pH 7.8, 5 mM CaCl2 and 0.1M NaCl at 4° C. for approximately 20 hours. The fusions were incubated with a 1 to 100 molar (enzyme to substrate) ratio of bovine thrombin obtained from Boehringer Mannheim (Indianapolis, Ind.) at room temperature (about 23° C.). The incubation was stopped after about 4 hrs. by freezing the cleavage mixture. The cleavage mixture was analyzed and purified on a C-18 analytical column as previously described for API and APIV fusions. About 25% of the theoretical APIII and 80% of the APIV were released following thrombin cleavage. Both APIII and APIV were bioactive in the chick rectum relaxation assay conducted in accordance with previously described methods. The N-terminal sequence of the APIII and the APIV released from the fusion proteins also confirmed the site-specific release of these peptides from the fusion proteins.

Expanded Disclosure

FIG. 12 depicts a plot of the hydropathicity of the recA protein.

As previously discussed, the present invention relates to the bacterial production of heterologous proteins or peptides by means of a fusion protein comprising an endogenous protein or fragment thereof, a trigger signal and a desired peptide or protein. In one important embodiment, the present invention relates to the bacterial production of atrial peptides.

This expanded disclosure describes certain discoveries made with respect to the endogenous carrier protein recA which, in the foregoing embodiments, was demonstrated to be a preferred carrier in the fusion protein constructs employed to bacterially produce such desired peptides as atrial peptides. Specifically, as previously described, the recA protein provided a means for producing such proteins as atrial peptides in bacteria at high levels (e.g. 10 to 30% of the total bacterial protein), in a stably accumulated form (e.g. a fusion protected from bacterial degradation) and in a form which provided a facile means for isolating both the recA-containing fusion and desired peptide free from bacterial proteins.

Based upon the unexpected preferential cleavage of a junction site V8 protease trigger signal in bacterially produced fusion proteins comprising a recA protein, a junction site Glu residue and an atrial peptide, and the factor Xa and thrombin mediated site-specific release of atrial peptides from fusion proteins comprising a recA protein, a junction site factor Xa or thrombin trigger signal and an atrial peptide, the following theory of mechanism was proposed. It is believed that the conformation of bacterially produced recA-containing fusion proteins renders the trigger signal-containing junction site available for subsequent endopeptidase cleavage.

The availability of the junction site trigger signal for interaction with the selected endopeptidase is a critical requirement if the site-specific release of a desired peptide from the fusion protein is to be achieved. Additionally, in one preferred embodiment employing the endopeptidase V8 protease, the observed preferred cleavage of the junction site trigger signal over the numerous (e.g. about 31) internal recA V8 protease trigger signals provides a means for subsequently isolating such peptides as atrial peptides substantially free from both bacterial proteins and the endogenous (recA) carrier protein. The selective isolation of the desired peptide would be much more costly and time consuming had the junction-site trigger signal not been preferentially cleaved by V8 protease. Specifically, cleavage of internal recA V8 protease sites results in the generation of multiple peptide fragments from which the desired peptide would have to be isolated. The selective cleavage at the junction site allows a rapid, inexpensive size fractionation of the desired peptide substantially free from the endogenous (recA) carrier protein. Additionally, the fusion protein to be cleaved with the selected endopeptidase must necessarily be soluble or solubilizable under conditions which permit endopeptidase cleavage.

It is believed that the conformation of the bacterially produced recA-containing fusion proteins is predominantly determined by the conformation of the recA protein as the recA protein constitutes about 90% (by amino acid composition) of the fusion protein.

Furthermore, it is believed that this conformation renders recA-containing fusion proteins soluble or readily solulizable and renders the junction site available for endopeptidase cleavage. Indeed, as described more fully herein, it was discovered that selective regions of the recA protein constitute highly hydrophillic regions and that these hydrophillic regions afford a protein conformation which renders the junction site trigger signal preferentially available for endopeptidase interaction and cleavage. Additionally, these regions of the recA protein were discovered to affect the solubility of bacterially produced recA-containing fusion proteins.

Employing monoclonal antibodies directed to the recA protein, it was first determined that a recA fragment from about amino acid residue 260 to about 330 was the most frequently identified region. Typically, very hydrophillic regions of a protein are often the most immunogenic regions as such regions are in contact with aqueous solvent and thus are available for presentation to the immune system. As shown in FIG. 12, which depicts a plot of the hydropathicity of the recA protein, the longest region of relatively uninterrupted hydrophillicity is from about residue 280 to about 353.

Thus, recA-containing fusion proteins comprising hydrophillic regions of the recA protein are predicted to be produced as soluble proteins in bacteria or soluble under endopeptidase cleavage conditions. Such fusion proteins would comprise recA residues from about 260 to about 330 or from about 280 to about 352 or 353 or from about 260 to about 352. Additionally, a junction site trigger signal covalently joined to recA amino acids in these hydrophillic regions is predicted to be exposed to solvent and thereby available for interaction with a given endopeptidase.

These predictions were confirmed in the previously described preferred embodiments comprising 100% recA, a V8 protease, factor Xa or thrombin trigger signal and an atrial peptide. Specifically, all preferred embodiments comprise hydrophillic recA regions and were demonstrated to be produced in bacteria as soluble proteins or were readily soluble by renaturation out of a denaturing buffer such as urea and furthermore, allowed the site-specific release of such proteins as atrial peptides by endopeptidase cleavage. Thus, it was discovered that fusion proteins comprising hydrophillic recA residues joined to a desired peptide by an endopeptidase trigger signal are particularly well suited for a method of bacterially producing a desired peptide employing an enzyme-mediated site-specific release of such desired peptides.

It is further believed that any endopeptidase trigger signal recognized by such endopeptidases as Trypsin, Plasmin, Enterkinase, Kallikrein, Urokinase, Tissue Plasminogen Activator, Clostripain, Chymotrypsin, Pepsin, Chymosin, Collagenase, Russell's Viper Venom Protease, Postproline cleaving enzyme, V8 Protease, Thrombin and factor Xa. Preferred endopeptidase trigger signals include these for V8 protease, factor Xa and thrombin. The preferred V8 protease trigger signal comprises Glu. The preferred factor Xa trigger signal comprises Glu-Gly-Arg, and the preferred thrombin trigger signal is derived from an amino acid sequence contained within atriopeptigen. The atriopeptigen-derived thrombin trigger signal is Arg-Ala-Leu-Leu-Ala-Gly-Pro-Arg. Also operable in the thrombin-mediated release of atrial peptides is the trigger sequence Gly-Pro-Arg. The former extended thrombin trigger sequence is most preferred.

Expanded Example 1

This example demonstrates the construction of an expression vector capable of directing the expression in such bacteria as *E. coli*, of a fusion protein comprising a recA fragment-Glu-APIII. The recA fragment contained amino acids 1 through 50 and 260 through 352.

The first step was to create a plasmid containing the recA promoter and codons for the recA amino acids 1 to 50. To accomplish this task, a double-stranded oligonucleotide linker containing a Bam HI site and having the sequence:

```
5'-GGATCCGC-3'
   -CGCCTAGG-
``` was inserted into the unique SstII site in pDR1461. pDR1461 is shown in FIG. 4. The unique SstII site is located between the BamHI site and upstream (i.e. 3') from the 70% recA gene. The resultant modified pDR1461 plasmid was then digested with BamHI and religated thereby causing a deletion of plasmid DNA from the BamHI site to the SstII site. The resultant plasmid was designated pMON2537. pMON2537 was digested with EcoRI and the sticky ends thereby created filled in with polI (*E. coli* polymerase I, Klenow fragment) as previously described, and then cut with EcoRV followed by S1 nuclease treatment and thereafter the plasmid was religated to form a new plasmid designated pMON2541. The S1 nuclease treatment results in a deletion of recA sequences from the EcoRV site to the EcoRI site. pMON2541 contained a recA promoter and codons for the first 50 amino acids of recA (i.e. amino acids 1–50).

A plasmid containing the codons for the recA amino acids 260–352 was then constructed as follows. Plasmid pMON6152, shown in FIG. 10, was cut with XbaI, the sticky-ends filled-in with polI and a HindIII linker containing the sequence:

```
5'-CAAGCTTG-3'
   -GTTCGAAC-
``` was then ligated thereto. Thereafter the plasmid was covalently closed with T4 DNA ligase and then cut with BamHI and HindIII. The BamHI/HindIII fragment containing the gene coding for 100% recA-Glu-APIII was isolated by gel electrophoresis by conventional methods and then inserted into pUC8 previously cleaved with BamHI and HindIII. The resultant pUC8 plasmid containing the gene for 100% recA-Glu-APIII was designated pMON2770.

The EcoRI site at the junction of recA and APIII was then removed by converting the junction site Glu codon to an Asp codon by oligonucleotide-directed site-specific mutagenesis as follows. pMON2770 was cut with BamHI and HindIII and the isolated BamHI/-HindIII fragment containing the gene for 100% recA-Glu-APIII inserted into M13mp18 RF DNA previously cut with BamHI and HindIII. The primer for mutagenesis was the following single-stranded DNA sequence:

```
5'-CAGCTGGATTCGAAGTCGTTAG-3'
```

The mutagenesis was conducted in accordance with previously described procedures and resulted in the following coding sequence change:

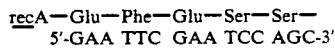
recA—Glu—Phe—Glu—Ser—Ser—
    5'-GAA TTC GAA TCC AGC-3' was converted to:

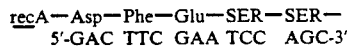
recA—Asp—Phe—Glu—SER—SER—
    5'-GAC TTC GAA TCC AGC-3'

The resultant M13mp18 RFDNA containing the newly altered junction site sequence was designated pMON2780. pMON2780 was then cut with EcoRI and HindIII thereby generating a HindIII/EcoRI restriction fragment containing the codons for recA amino acids 260-352 with the Glu to Asp change, Glu and APIII. pMON2541 was then cleaved with BamHI and EcoRI to generate a BamHI/EcoRI restriction fragment containing the recA promoter and codons for the recA amino acids 1-50. The HindIII/EcoRI fragment from pMON2780 and Bam HI/EcoRI fragment from pMON2541 were then both inserted into pUC8 previously cut with BamHI and HindIII. The resultant pUC8 plasmid containing a gene for a fusion protein comprising recA 1-50 and 260-352 (with the Glu to Asp change)-Glu-APIII was designated pMON2790.

Expanded Example 2

This example demonstrates the expression in bacteria of a fusion protein comprising 40% recA (e.g. amino acids 1-50 and 260-352)-Glu-APIII and the subsequent purification of APIII therefrom.

*E. coli* JM101 cells were transformed with pMON2790 and subsequently induced by the addition of nalidixic acid to the culture media, all as previously described.

The fusion proteins were purified as follows. The recA (1-50/260-352)-Glu-APIII was produced as an aggregate contained in refractile bodies and required a denaturing agent such as urea for solubilization. This fusion protein binds to anion exchange resins such as Pharmacia MonoQ® HR10/10 at pH 7.0-9.0 can be eluted therefrom with 100-300 mM NaCl depending upon the pH. The Pharmacia MonoQ® HR10/10, hereinafter MonoQ® was prepared for use by equilibration with 50 mM Tris-Cl, 6.0 M urea, pH 8.0, at 25° C. All buffers used in the process contained 6.0M urea. A 5 gram quantity of cell paste was resuspended in 50 ml of distilled/deionized water at 8° C. and sonicated using a Heat Systems-Ultrasonic, Inc. Model 10-375, containing a ¾ inch tip for a total of 3 minutes in 1 minute increments. The sonicated suspension was then centrifuged at 5000×g. for 10 minutes. The supernatant was discarded and the solid pellet was resuspended in 50 ml of 50 mM sodium acetate pH 5.5, at 8° C., and centrifuged at 7500×g. for 10 minutes. This step was repeated a total of 4 times. The solid pellet was dissolved in 10-20 ml of 9.0M urea, 50 mM Tris-Cl, pH 8.0, at 8° C. and centrifuged at 10,000×g. The supernatant was decanted from the pellet and applied to the MonoQ® column at a flow rate of about ml per minute. A linear gradient of increasing NaCl concentration ranging from about 100 mM to 300 mM NaCl was applied to the column and fractions containing about 4 ml were collected, and was shown to resolve the fusion proteins from about 90% of all *E. coli* proteins. Elution of the proteins from the column was monitored by ultraviolet absorbance at 280 nm and by electrophoretic analysis. Those fractions containing fusion protein were combined. The fusion protein elutes at about 200mM NaCl.

The ability to solubilize and purify the 40% recA containing fusion proteins by amino-ethyl (e.g. anion exchange) chromatography demonstrates that the 40% recA-containing fusion proteins retain similar solubility and charge properties of the 100% recA-containing fusion proteins.

Cleavage of the purified fusion proteins with V8 protease was conducted as described above for the 100% recA-Glu-atrial peptide fusion proteins. The release of APIII from the 40% recA-containing fusion proteins by V8 protease cleavage was about 80% by HPLC analysis conducted as previously described. The APIII peptide so released was bioactive in the chick rectum relaxation assay conducted in accordance with previously described methods.

The preferred cleavage of the V8 junction site trigger signal in the 40% recA-containing fusion proteins demonstrate that very large (i.e. 110 amino acid) deletions in the recA protein can be made without altering the overall shape and processing characteristics of the recA protein.

References

1. Austen and Smith (1976) *Biochem. and Biophys. Res. Comm.* 72:411
2. Behrens and Brown (1976) *Federation Proceedings* 35:Abstract No. 611
3. Bolivar et al. (1977) *Gene* 2:95
4. Chirikjian, J. and Papas, T. eds. (1981) Elsever/-North Holland, New York, pp. 383-415
5. Cleveland et al. (1977) *J. Biol. Chem* 252:1102-1106
6. Craig, R.K. and Hall, L. (1983) *Genetic Engineering* 4 ed. R. Williamson, Academic Press
7. Currie et al. (1983) *Science* 221:71-73
8. deBold et al. (1983) *Fed. Proc.* 42(3):Abstract 1870, page 611

9. Eitner et al. (1982) *Mol. Gen. Genet.* 185:481.
10. deBold and Flynn (1983) *Life Sci.* 33:297–302
11. Feinstein, S. et al. (1983) *Nucleic Acids Research* 11:2927–2941
12. Fiers, W. et al. (1976) *Nature* 260:500
13. Germino, J. and Bastia, D. (1984) *Proc. Nat'l. Acad. Sci. U.S.A.* 81:4692–4696
14. Goeddel et al. (1979) *Biochemistry* 76:101–110
15. Harris, T.J.R. (1983) in *Genetic Engineering* Vol. 4 (ed. Williamson, R.) p. 127–185, Academic London
16. Hausinger and Howard (1982) *J. Biol. Chem.* 7:2483–2490
17. Hershfield et al. (1974) *Proc. Nat'l. Acad. Sci., U.S.A.* 71:3455
18. Houmard and Drapeau (1972a) *Proc. Nat'l. Acad. Sci. U.S.A.* 69:3506–3509
19. Houmard and Drapeau (1972b) *J. Biol. Chem.* 7:6720–6726
20. Hunkapiller et al. (1983a) *Methods in Enzymology* 91:399–413
21. Hunkapiller et al. (1983b) *Methods in Enzymology* 91:486–493
22. Ikemura, T. (1982) *J. Mol. Biol.* 158:573–597
23. Itakura et al. (1977) *Science* 198:1056–1063
24. Johnson, J.S. (1983) *Science* 219:632–637
25. Keener, S., McNamee, K. and McEntee, K. (1984) *J. Bacteriol.* 160:153–160.
26. Laemmli (1970) *Nature* 227:680–685
27. Loenen et al. (1980) *Gene* 10:249
28. Magnusson, S. (1971) in *The Enzymes* ed. Paul D. Boyer, vol. 3, pages 278–321.
29. Magnusson, S. et al.(1975) in *Proteases and Biological Control*; Reich, E., Rifkin, D.B. and Shaw, E., eds. p.123–149; Cold Spring Harbor Laboratories, New York.
30. Maniatis, Fritsch and Shambrook, eds. (1982) *Molecular Cloning: A Laboratory Manual*
31. Messing et al. (1982) *Gene* 19269
32. Messing et al. (1983) *Methods in Enzymol.* 101:20
33. Miller, J. H. (1972) *Exps. in Mol. Gen.*, Cold spring Harber Publications, p. 431
34. Misono, K. S. et al. (1984) *Biochem. Biophys. Res. Comm.* 123:444–451
35. Nagai and Thogersen (1984) *Nature* 309:810–812
36. Norris et al. (1983) *Nucleic Acid Research* 11:5103–5112
37. Pitts, R.F. (1974) *Physiology of the Kidney and Body Fluids*, 3rd ed., Chicago, Year Book Medical Publishers, pp. 242–258
38. Rao et al. (1979) *Gene* 7:79
39. Rosenberg, M. et al. (1968) *J. Mol. Biol* 31:487–505
40. Rutter, W.J. (1979) in *Recombinant DNA and Genetic Experiment* eds. Morgan, J. and Whelan, W.J.
41. Sancar, A. and Rupp, D. (1979) *Proc. Nat'l. Acad. Sci. U.S.A.* 76:3144–3148
42. Sancar et al. (1980) *Proc. Nat'l. Acad. Sci. U.S.A.*
43. Sanger et al. (1977) *Proc. Nat'l. Acad. Sci., . U.S.A.* 74:5463–77:2611–2615
44. Seidah, N.G. et al. (1984) *Proc. Nat'l. Acad. Sci. U.S.A.* 81:2640–2644
45. Shine et al. (1980) *Nature* 285:456–461
46. Soberon et al. (1978) *Gene* 4:121
47. Stephien et al. (1983) *Gene* 24:289–297
48. Sussenfeld, H.M. and Bastia, S.J. (1984) *Biotechnology* Jan., 76–81
49. Tanaka et al. (1982) *Nucleic Acid Research* 10:1741–1754
50. Trippodo et al. (1982) *Proc. Soc. Exp. Biol. Med.* 170:502–508
51. White and Samson (1954) *J. Lab. Clin. Med.* 43:475–478
52. Witkin, E.M. (1975) *Bacteriol. Rev.* 4D:869–097
53. Zoller and Smith (1982) *Nucleic Acid Research* 10:6487–6500
54. Zoller and Smith (1983) *Meth. Enzymol.* 100:468–500

We claim:

1. A method for producing a heterologous peptide in bacteria which comprises expressing DNA comprising a fusion protein to produce a fusion protein in bacteria, said fusion protein comprising a heterologous peptide not susceptible to V8 endopeptidase cleavage linked to *E. coli* recA protein at a Glu-Ser junction site, wherein both the *E. coli* recA protein and the junction site have a V8 endopeptidase Glu-Ser cleavage site; recovering said fusion protein from the bacteria; treating said fusion protein with V8 endopeptidase such that the endopeptidase cleavage side at said Glu-Ser junction site is preferentially cleaved while the V8 endopeptidase cleavage site in the recA protein is substantially intact, and obtaining therefrom said desired heterologous peptide.

2. The method of claim 1 wherein said heterologous peptide is an atrial peptide.

3. The method of claim 2 wherein said atrial peptide is selected from a group consisting of atrial peptide I, atrial peptide III and atrial peptide IV.

4. The method of claim 1 wherein said DNA further comprises a plasmid.

5. The method of claim 4 wherein said plasmid is selected from the group consisting of pMON6152, pMON6154, and pMON6159.

6. A DNA segment encoding sequentially a promoter that functions in bacteria, a ribosome binding site, a *E. coli* recA protein, a Glu-Ser junction site which comprises a V8 endopeptidase cleavage site, a heterologous peptide not susceptible to V8 endopeptidase cleavage and a translation stop signal.

7. The DNA segment of claim 6 wherein said heterologous peptide is an atrial peptide.

8. The DNA segment of claim 7 wherein said atrial peptide is selected from the group consisting of atrial peptide I, atrial peptide III and atrial IV.

9. A recombinant vector selected from the group consisting of a bacterial plasmid and a bacteriophage, comprising the DNA segment of claim 6.

10. A transformed bacterial strain comprising the DNA segment of claim 6.

11. A method for producing atrial peptides in Gram-negative bacteria comprising:
   a. causing expression of DNA which expression results in the production of fusion protein comprising a *E. coli* recA protein, a Glu-Ser junction site comprising a V8 endopeptidase cleavage site and an atrial peptide;
   b. isolating the fusion protein;
   c. cleaving the fusion protein with V8 endopeptidase at the Glu-Ser junction site; and
   d. obtaining therefrom the atrial peptide.

12. A method of claim 11 wherein the atrial peptide is selected from a group consisting of APl, APIII and APIV.

13. The method of claim 11 wherein the recA protein comprises a hydrophilic region of the recA protein.

14. The method of claim 13 wherein the hydrophilic region comprises the amino acids from about 280 to about 353.

15. The method of claim 13 wherein the hydrophilic region comprises the amino acids from about 260 to about 330.

16. The method of claim 13 wherein the hydrophilic region comprises the amino acids from about 260 to about 353.

17. The method of claim 11 wherein the recA protein comprises 100% of the recA gene product.

18. The method of claim 11 wherein the recA protein comprises 40% of the recA gene product.

19. The method of claim 18 wherein the 40% recA comprises a hydrophilic region of the recA protein.

20. An expression vector comprising pMON6163.

21. An expression vector comprising pMON6164.

22. An expression vector comprising pMON6160.

23. An expression vector comprising pMON6166.

24. An expression vector comprising pMON2790.

* * * * *